United States Patent [19]

Parsons et al.

[11] Patent Number: 5,310,901

[45] Date of Patent: May 10, 1994

[54] O-HETEROARYL, O-ALKYLHETEROARYL, O-ALKENYLHETEROARYL AND O-ALKYNLHETEROARYLRAPAMYCIN DERIVATIVES

[75] Inventors: William H. Parsons, Edison; Peter J. Sinclair, Highland Park; Frederick Wong, Glen Ridge; Matthew J. Wyvratt, Mountainside, all of N.J.

[73] Assignee: Merck & Co., Inc., Rahway, N.J.

[21] Appl. No.: 26,926

[22] Filed: Mar. 5, 1993

[51] Int. Cl.$^5$ .................. A61K 31/395; C07D 471/18
[52] U.S. Cl. .............................................. 540/456
[58] Field of Search ........................ 540/456; 514/291

[56] References Cited

U.S. PATENT DOCUMENTS

| | | |
|---|---|---|
| 3,929,992 | 12/1975 | Sehgal et al. |
| 4,650,803 | 3/1987 | Stella et al. ............ 514/291 |
| 5,100,883 | 3/1992 | Schiehser ............ 514/183 |
| 5,102,876 | 4/1992 | Caufield ............ 514/183 |
| 5,118,677 | 6/1992 | Caufield ............ 514/183 |
| 5,118,678 | 6/1992 | Kao et al. ............ 514/183 |
| 5,120,725 | 6/1992 | Kao et al. ............ 514/183 |
| 5,120,727 | 6/1992 | Kao et al. ............ 514/183 |
| 5,120,842 | 6/1992 | Failli et al. ............ 540/452 |
| 5,138,051 | 8/1992 | Hughes et al. ............ 540/456 |
| 5,151,413 | 9/1992 | Caufield et al. ............ 514/63 |
| 5,162,333 | 11/1992 | Failli et al. ............ 514/291 |
| 5,162,334 | 11/1992 | Goulet et al. ............ 514/291 |
| 5,169,851 | 12/1992 | Hughes et al. ............ 514/291 |

FOREIGN PATENT DOCUMENTS

| | | | |
|---|---|---|---|
| 0227355 | 7/1987 | European Pat. Off. ............ 514/291 |
| 0516347 | 12/1992 | European Pat. Off. ............ 514/291 |
| 2245891 | 1/1992 | United Kingdom ............ 514/291 |
| WO89/05304 | 6/1989 | World Int. Prop. O. ............ 540/456 |
| WO91/02736 | 3/1991 | World Int. Prop. O. ............ 540/456 |
| WO91/13889 | 9/1991 | World Int. Prop. O. ............ 540/456 |
| WO92/05179 | 4/1992 | World Int. Prop. O. ............ 540/456 |
| WO92/14737 | 9/1992 | World Int. Prop. O. ............ 540/456 |
| WO92/21341 | 10/1992 | World Int. Prop. O. ............ 540/456 |
| WO92/20688 | 11/1992 | World Int. Prop. O. ............ 540/456 |
| WO93/05058 | 3/1993 | World Int. Prop. O. ............ 540/456 |
| WO93/05059 | 3/1993 | World Int. Prop. O. ............ 540/456 |

OTHER PUBLICATIONS

Finday et al., Can. J. Chem., 58, 579–590 (1980).

Primary Examiner—Robert T. Bond
Attorney, Agent, or Firm—Charles M. Caruso; J. Eric Thies

[57] ABSTRACT

O-Heteroaryl, O-alkylheteroaryl, O-alkenylheteroaryl and O-alkynylheteroarylrapamycin derivatives of the general structural Formula I:

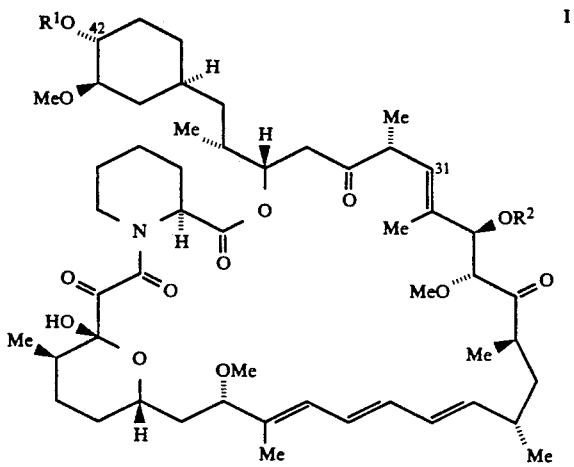

have been prepared from suitable precursors by alkylation and/or arylation at C-42 and/or C-31. These compounds are useful in a mammalian host for the treatment of autoimmune diseases and diseases of inflammation, infectious diseases, the prevention of rejection of foreign organ transplants and the treatment of solid tumors.

5 Claims, No Drawings

O-HETEROARYL, O-ALKYLHETEROARYL, O-ALKENYLHETEROARYL AND O-ALKYNLHETEROARYLRAPAMYCIN DERIVATIVES

SUMMARY OF THE INVENTION

The present invention is related to O-heteroaryl, O-alkylheteroaryl, O-alkenylheteroaryl and O-alkynlheteroarylrapamycin derivatives which are useful in a mammalian host for the treatment of autoimmune diseases (such as juvenile-onset or recent-onset diabetes mellitus, multiple sclerosis, rheumatoid arthritis, liver disease, posterior uveitis, allergic encephalomyelitis, and glomerulonephritis), diseases of inflammation, infectious diseases (particularly fungal infections), the prevention of rejection of foreign organ transplants, e.g. bone marrow, kidney, liver, heart, skin, small-bowel, and pancreatic-islet-cell transplants, and the treatment of solid tumors.

More particularly, this invention relates to compounds of the general structural Formula I:

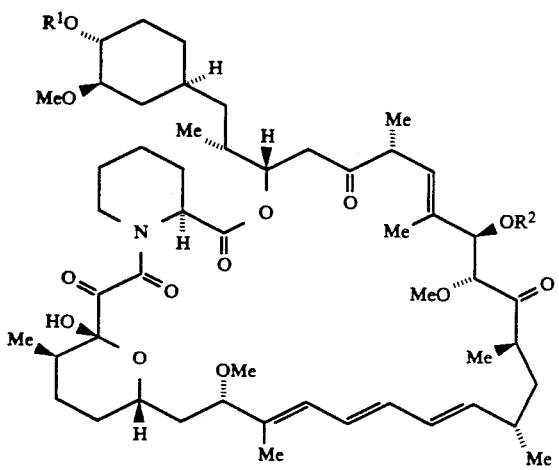

wherein $R^1$ and $R^2$ are hereinafter defined.

This invention also relates to pharmaceutical compositions containing the compounds, and to a method of use of the present compounds and other agents for the treatment and prevention of certain afflictions, diseases and illnesses.

BACKGROUND OF THE INVENTION

Rapamycin characterized by Findlay and co-workers in 1978 is a 35-membered macrolide isolated from *S. hygroscopicus* (*Can. J. Chem.*, 1978, 56, 2491, *J. Antibiotics*, 1975, 28, 721, U.S. Pat. No. 3,929,992, issued Dec. 30, 1975, U.S. Pat. No. 3,993,749, issued Nov. 23, 19975. Rapamycin has been found to have antifungal activity, particularly against *Candida albicans*, both in vitro and in vivo (*J. Antibiotics*, 1978, 31, 539).

Rapamycin alone (U.S. Pat. No. 4,885,171) or in combination with picibanil (U.S. Pat. No. 4,401,653) has been shown to have antitumor activity. R. Martel et al. (*Can. J. Physiol, Pharmacol*, 55, 48 (1977) disclosed that rapamycin is effective in an experimental allergic encephalomyelitis model, a model for multiple sclerosis; in an adjuvant arthritis model, a model for rheumatoid arthritis; and effectively inhibited the formation of IgE-like antibodies.

The immunosuppressive effects of rapamycin have been disclosed (*FASEB* 3, 3411 (1989); *Med. Sci. Res.*, 1989, 17, 877). Cyclosporin A and FK-506, other macrocyclic molecules, also have been shown to be effective as immunosuppressive agents, therefore useful in preventing transplant rejection (*FASEB* 3, 3411 (1989); *FASEB* 3, 5256 (1989); and *Lancet* 1183 (1978)).

Fujisawa United States patents (U.S. Pat. No. 4,929,611, issued May 29, 1990 and U.S. Pat. No. 4,956,352, issued Sep. 11, 1990) disclose the use of FK-506-type compounds in treating resistance to transplantation. A Sandoz European patent application (EPO Publication No. 0.315,978) discloses the use of FR-900506 and related compounds in the topical treatment of inflammatory and hyperproliferative skin diseases and of cutaneous manifestations of immunologically-mediated illness. A Fisons World patent application (PCT Publication WO 90/14826) discloses the use of FR-900506 and related compounds in the treatment of reversible obstructive airways disease, particularly asthma. A Fujisawa European patent application (EPO Publication No. 0,423,714) discloses the use of FK-506 and derivatives as hair revitalizing agents. Various studies have suggested the efficacy of FK-506 in the treatment of a number of ailments, including rheumatoid arthritis (C. Arita, et al., *Clincial exp. Immunol.*, 1990, 82, 456–461; N. Inamura, et al., *Clin. Immunol. Immunopathol*, 1988, 46, 82–90), recent-onset diabetes (N. Murase, et al., *Diabetes*, 1990, 39, 1584–86; N. Murase, et al., *Lancet*, 1990, 336, 373–74), posterior uveitis (H. Kawashima, *Invest. Ophthalmul. Vis. Sci.*, 1988, 29, 1265–71), Hepatic injury associated with ischemia (M. Sakr, et al., *Life Sci.*, 1990, 47, 687–91) allergic encephalomyelitis (K, Deguchi, et al., *Brain Nerve*, 1990, 42, 391–97), glomerulonephritis (J. McCauley, et al., *Lancet*, 1990, 335, 674), systemic lupus erythematosus (K. Takabayashi, et al., *Clin. Immunol. Immunopathol.*, 1989, 51, 110–117), multidrug resistance (M. Naito, et al., *Cancer Chemother. Pharmacol.*, 192, 29, 195–200), inflammation of mucosa and blood vessels (PCT Publication WO 91/17754), cytomegalovirus infection (UK Publication GB 2,247,620A), and idiopathic thrombocytophenic purpura and Basedow's disease (PCT Publication WO 91/19495).

Mono- and diacylated derivatives of rapamycin (esterified at the 31 and 42 positions) have been shown to be useful as antifungal agents (U.S. Pat. No. 4,316,885) and have been used as water soluble prodrugs of rapamycin (U.S. Pat. No. 4,650,803 and PCT Patent Publication WO 92/21341). Reduction products of rapamycin have been prepared (U.S. Pat. Nos. 5,102,876 and 5,138,051). Derivatives of rapamycin at the 31 and 42 positions which have been disclosed include: carboxylic acid esters (PCT Patent Publication WO92/05179); carbamates (U.S. Pat. No. 5,118,678); amide esters (U.S. Pat. No. 5,118,677); fluorinated esters (U.S. Pat. No. 5,100,883); acetals (U.S. Pat. No. 5,151,413); and silyl ethers (U.S. Pat. No. 5,120,842). In addition, bicyclic derivatives of rapamycin connected via the 31, 42 positions (U.S. Pat. No. 5,120,725) and rapamycin dimers connected via the 42 position (U.S. Pat. No. 5,120,727) have been disclosed. Various aryl(lower alkyl) and heteroaryl derivatives of FK-506 type compounds have also been disclosed (UK Patent Publication No. GB 2,245,891A). O-Aryl, O-alkyl, O-alkenyl and O-alkynyl derivatives of FK-506 type compounds have been disclosed (EPO Patent Publication No. 0,515,071).

DETAILED DESCRIPTION OF THE INVENTION

A. Scope of the Invention

The novel compound of this invention has structural Formula I:

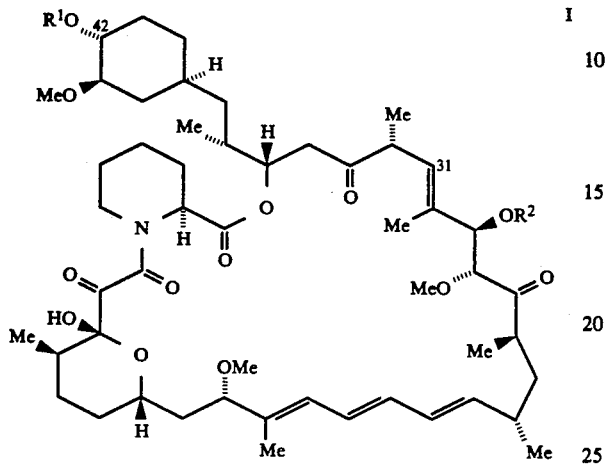

or a pharmaceutically acceptable salt thereof, wherein:

$R^1$ is selected from:

(1) heteroaryl;

(2) substituted heteroaryl in which the substituents are X, Y and Z;

(3) heteroaryl-$C_{1-10}$alkyl;

(4) substituted heteroaryl-$C_{1-10}$alkyl in which the heteroaryl group is substituted by X, Y and Z and the alkyl portion may be substituted with one or more of the substituent(s) selected from:
   (a) hydroxy,
   (b) oxo,
   (c) $C_{1-6}$-alkoxy,
   (d) aryl-$C_{1-3}$alkoxy,
   (e) substituted aryl-$C_{1-3}$alkoxy, in which the substituents on aryl are X, Y and Z,
   (f) unsubstituted or substituted aryloxy, in which the substituents on aryl are X, Y and Z,
   (g) —OCO—$C_{1-6}$alkyl,
   (h) —$NR^6R^7$, wherein $R^6$ and $R^7$ are independently selected from
      (i) hydrogen,
      (ii) $C_{1-10}$alkyl unsubstituted or substituted with one or more of the substituent(s) selected from:
         (a') aryl, which is unsubstituted or substituted with X, Y and Z,
         (b') heteroaryl, which is unsubstituted or substituted with X, Y and Z,
         (c') —OH,
         (d') $C_{1-6}$alkoxy,
         (e') —$CO_2H$,
         (f') —$CO_2$—$C_{1-6}$alkyl,
         (g') —$C_{3-7}$cycloalkyl, and
         (h') —$OR^{11}$,
      (iii) $C_{3-10}$alkenyl unsubstituted or substituted with one or more of the substituent(s) selected from:
         (a') aryl, which is unsubstituted or substituted with X, Y and Z,
         (b') heteroaryl, which is unsubstituted or substituted with X, Y and Z,
         (c') —OH,
         (d') $C_{1-6}$alkoxy,
         (e') —$CO_2H$,
         (f') —$CO_2$—$C_{1-6}$alkyl,
         (g') —$C_{3-7}$cycloalkyl, and
         (h') —$OR^{11}$,
      (iv) or where $R^6$ and $R^7$ and the N to which they are attached may form an unsubstituted or substituted 3–7-membered heterocyclic ring which may include one or two additional heteroatoms independently selected from the group consisting of O, $S(O)_p$, $NR^{14}$, wherein $R^{14}$ is hydrogen or $C_{1-6}$ alkyl unsubstituted or substituted by phenyl, and p is 0, 1 or 2, such as morpholine, thiomorpholine, piperidine, or piperizine,
   (i) —$NR^6CO$—$C_{1-6}$alkyl-$R^7$, wherein $R^6$ and $R^7$ are as defined above,
   (j) —$NR^6CO_2$—$C_{1-6}$alkyl-$R^7$,
   (k) —$NR^6CONR^6R^7$,
   (l) —$OCONR^6R^7$,
   (m) —$COOR^6$,
   (n) —CHO,
   (o) aryl,
   (p) substituted aryl in which the substituents are X, Y and Z,
   (q) —$OR^{11}$, and
   (r) —$S(O)_p$—$C_{1-6}$alkyl;

(5) heteroaryl-$C_{1-10}$alkyl wherein one or more of the alkyl carbons is replaced by a group selected from: —$NR^6$—, —O—, —$S(O)_p$—, —$CO_2$—, —$O_2C$—, —$CONR^6$—, —$NR^6CO$—, —$NR^6CONR^7$—;

(6) substituted heteroaryl-$C_{1-10}$alkyl wherein one or more of the alkyl carbons is replaced by a group selected from: —$NR^6$—, —O—, —$S(O)_p$—, —$CO_2$—, —$O_2C$—, —$CONR^6$—, —$NR^6CO$—, and —$NR^6CONR^7$—, the heteroaryl group is substituted with X, Y, and Z, and the alkyl group may be substituted with one or more of the substituent(s) selected from:
   (a) hydroxy,
   (b) oxo,
   (c) $C_{1-6}$alkoxy,
   (d) aryl-$C_{1-3}$alkoxy,
   (e) substituted aryl-$C_{1-3}$alkoxy, in which the substituents on aryl are X, Y and Z,
   (f) unsubstituted or substituted aryloxy, in which the substituents on aryl are X, Y and Z,
   (g) —OCO—$C_{1-6}$alkyl,
   (h) —$NR^6R^7$, wherein $R^6$ and $R^7$ are as defined above,
   (i) —$NR^6CO$—$C_{1-6}$alkyl-$R^7$,
   (j) —$NR^6CO_2$—$C_{1-6}$alkyl-$R^7$,
   (k) —$NR^6CONR^6R^7$,
   (l) —$OCONR^6R^7$,
   (m) —$COOR^6$,
   (n) —CHO,
   (o) aryl,
   (p) substituted aryl in which the substituents are X, Y and Z,
   (q) —$OR^{11}$, and
   () —$S(O)_p$—$C_{1-6}$alkyl;

(7) heteroaryl-$C_{3-10}$alkenyl wherein alkenyl contains one to four double bonds;

(8) heteroaryl-$C_{3-10}$alkenyl wherein alkenyl contains one to four double bonds and wherein one or more of the alkyl carbons is replaced by a group selected from: —$NR^6$—, —O—, —$S(O)_p$—, —$CO_2$—, —O₂C—, —CONR⁶—, —NR⁶CO—, and —NR⁶CONR⁷—;

(9) substituted heteroaryl-C₃₋₁₀alkenyl wherein alkenyl contains one to four double bonds and wherein one or more of the alkyl carbons may e replaced by a group selected from: —NR⁶—, —O—, —S(O)$_p$—, —CO₂—, —O₂C—, —CONR⁶—, —NR⁶CO—, and —NR⁶CONR⁷, the heteroaryl group is substituted with X, Y, and Z, and the alkyl group may be substituted with one or more of the substituent(s) selected from:
 (a) hydroxy,
 (b) oxo,
 (c) C₁₋₆alkoxy,
 (d) aryl-C₁₋₃alkoxy,
 (e) substituted aryl-C₁₋₃alkoxy, in which the substituents on aryl are X, Y and Z,
 (f) unsubstituted or substituted aryloxy, in which the substituents on aryl are X, Y and Z,
 (g) —OCO—C₁₋₆alkyl,
 (h) —NR⁶R⁷, wherein R⁶ and R⁷ as defined above,
 (i) —NR⁶CO—C₁₋₆alkyl, wherein R⁶ is as defined above,
 (j) —NR⁶CO₂—C₁₋₆alkyl,
 (k) —NR⁶CONR⁶R⁷,
 (l) —OCONR⁶R⁷,
 (m) —COOR⁶,
 (n) —CHO,
 (o) aryl,
 (p) substituted aryl in which the substituents are X, Y and Z, and
 (q) —OR¹¹, and
 (r) —S(O)$_p$—C₁₋₆alkyl;

R² is selected from:
 (1) the definitions of R¹;
 (2) hydrogen;
 (3) phenyl;
 (4) substituted phenyl in which the substituents are X, Y and Z;
 (5) 1- or 2-naphthyl;
 (6) substituted 1- or 2-naphthyl in which the substituents are X, Y and Z;
 (7) biphenyl;
 (8) substituted biphenyl in which the substituents are X, Y and Z;
 (9) C₁₋₁₀alkyl;
 (10) substituted-C₁₋₁₀alkyl in which one or more substituent(s) is(are) selected from:
  (a) hydroxy,
  (b) oxo,
  (c) C₁₋₆alkoxy,
  (d) aryl-C₁₋₃alkoxy,
  (e) substituted aryl-C₁₋₃alkoxy, in which the substituents on aryl are X, Y and Z,
  (f) unsubstituted or substituted aryloxy, in which the substituents on aryl are X, Y and Z,
  (g) —OCO—C₁₋₆alkyl,
  (h) —NR⁶R⁷, wherein R⁶ and R⁷ are as defined above
  (i) —NR⁶CO—C₁₋₆alkyl-R⁷, wherein R⁶ and R⁷ are as defined above,
  (j) —COOR⁶, wherein R⁶ is as defined above,
  (k) —CHO,
  (l) phenyl,
  (m) substituted phenyl in which the substituents are X, Y and Z,
  (n) 1- or 2-naphthyl,
  (o) substituted 1- or 2-naphthyl in which the substituents are X, Y and Z,
  (p) biphenyl,
  (q) substituted biphenyl in which the substituents are X, Y and Z,
  (r) —OR¹¹, and
  (s) —S(O)$_p$—C₁₋₆alkyl;
 (11) C₃₋₁₀alkenyl;
 (12) substituted C₃₋₁₀alkenyl in which one or more substituent(s) is(are) selected from:
  (a) hydroxy,
  (b) oxo,
  (c) C₁₋₆alkoxy,
  (d) phenyl-C₁₋₃alkoxy,
  (e) substituted phenyl-C₁₋₃alkoxy, in which the substituents on phenyl are X, Y and Z,
  (f) —OCO—C₁₋₆alkyl,
  (g) —NR⁶R⁷, wherein R⁶ and R⁷ are as defined above
  (h) —NR⁶CO—C₁₋₆alkyl, wherein R⁶ is as defined above,
  (i) —COOR⁶, wherein R⁶ is as defined above,
  (j) —CHO,
  (k) phenyl,
  (l) substituted phenyl in which the substituents are X, Y and Z,
  (m) 1- or 2-naphthyl,
  (n) substituted 1- or 2-naphthyl in which the substituents are X, Y and Z,
  (o) biphenyl,
  (p) substituted biphenyl in which the substituents are X, Y and Z,
  (q) —OR¹¹, and
  (r) —S(O)$_p$—C₁₋₆alkyl;
 (13) C₃₋₁₀alkynyl;
 (14) substituted C₃₋₁₀alkynyl in which one or more substituent(s) is(are) selected from:
  (a) hydroxy,
  (b) oxo,
  (c) C₁₋₆alkoxy,
  (d) phenyl-C₁₋₃alkoxy,
  (e) substituted phenyl-C₁₋₃alkoxy, in which the substituents on phenyl are X, Y and Z,
  (f) —OCO—C₁₋₆alkyl,
  (g) —NR⁶R⁷, wherein R⁶ and R⁷ are as defined above,
  (h) —NR⁶CO—C₁₋₆alkyl, wherein R⁶ is as defined above,
  (i) —COOR⁶, wherein R⁶ is as defined above,
  (j) —CHO,
  (k) phenyl,
  (l) substituted phenyl in which the substituents are X, Y and Z,
  (m) 1- or 2-naphthyl,
  (n) substituted 1- or 2-naphthyl in which the substituents are X, Y and Z,
  (o) biphenyl,
  (p) substituted biphenyl in which the substituents are X, Y and Z,
  (q) —OR¹¹; and
 (15) —R¹¹;

R¹¹ is selected from:
 (a) —PO(OH)O⁻M⁺, wherein M⁺ is a positively charged inorganic or organic counterion,
 (b) —SO₃⁻M⁺,
 (c) —CO(CH₂)$_q$CO₂⁻M⁺, wherein Q is 1-3, and
 (d) —CO—C₁₋₆alkyl-NR⁶R⁷, wherein R⁶ and R⁷ are as defined above and the alkyl is unsubstituted or substituted with one or more substituents selected from:
(i) hydroxy,
(ii) $C_{1-6}$alkoxy,
(iii) —$NR^{16}R^{17}$, wherein $R^{16}$ and $R^{17}$ are independently selected from:
  (a′) hydrogen, and
  (b′) $C_{1-6}$alkyl,
(iv) —$COOR^6$, wherein $R^6$ is as defined above,
(v) phenyl,
(iv) substituted phenyl in which the substituents are X, Y and Z,
(vii) heteroaryl,
(viii) —SH, and
(ix) —S—$C_{1-6}$alkyl;

X, Y and Z independently are selected from:
(a) hydrogen,
(b) $C_{1-10}$alkyl, unsubstituted or substituted with one or more substituents selected from:
  (i) aryl,
  (ii) substituted aryl in which the substituents are X′, Y′ and Z′,
  (iii) heteroaryl,
  (iv) substituted heteroaryl in which the substituents are X′, Y′, and Z′,
  (v) unsubstituted or substituted aryloxy, in which the substituents on aryl are X′, Y′ and Z′.
  (vi) —$OR^6$,
  (vii) —$OR^{11}$,
  (viii) —$OCOR^6$,
  (ix) —$OCO_2R^6$,
  (x) —$NR^6R^7$,
  (xi) —CHO,
  (xii) —$NR^6COC_{1-6}$alkyl-$R^7$,
  (xiii) —$NR^6CO_2C_{1-6}$alkyl-$R^7$,
  (xiv) —$NR^6CONR^6R^7$,
  (xv) —$OCONR^6R^7$,
  (xvi) —$CONR^6R^7$,
(c) $C_{1-10}$alkyl wherein one or more of the alkyl carbons is replaced by a group selected from —$NR^6$—, —O—, —$S(O)_p$—, —$CO_2$—, —$O_2C$—, —$CONR^6$—, —$NR^6CO$—, —$NR^6CONR^7$—, —CO—, —CH(OH)—, alkenyl or alkynyl and the alkyl may be unsubstituted or substituted with one or more substituents selected from:
  (i) aryl,
  (ii) substituted aryl in which the substituents are X′, Y′ and Z′,
  (iii) heteroaryl,
  (iv) substituted heteroaryl in which the substituents are X′, Y′, and Z′,
  (v) unsubstituted or substituted aryloxy, in which the substituents on aryl are X′, Y′, and Z′,
  (vi) —$OR^6$,
  (vii) —$OR^{11}$,
  (viii) —$OCOR^6$,
  (ix) —$OCO_2R^6$,
  (x) —$NR^6R^7$,
  (xi) —CHO
  (xii) —$NR^6COC_{1-6}$alkyl-$R^7$,
  (xiii) —$NR^6CO_2C_{1-6}$alkyl-$R^7$,
  (xiv) —$NR^6CNHR^6R^7$,
  (xv) —$OCONR^6R^7$,
  (xvi) —$CONR^6R^7$,
(d) halogen,
(e) —$NR^6R^7$,
(f) —CN,
(g) —CHO,
(h) —$CF_3$,
(i) —$SR^8$, wherein $R^8$ is hydrogen, $C_{1-6}$alkyl, trifluoromethyl or phenyl,
(j) —$SOR^8$,
(k) —$SO_2R^8$,
(l) —$CONR^6R^7$,
(m) $R^9O(CH_2)_m$— wherein $R^9$ is hydrogen, $C_{1-6}$alkyl, hydroxy-$C_{2-3}$alkyl, —$CF_3$, phenyl, $R^{11}$ or naphthyl and m is 0, 1, 2, or 3,
(n) —$CH(OR^{12})(OR^{13})$, wherein $R^{12}$ and $R^{13}$ are $C_{1-3}$alkyl or taken together form an ethyl or propyl bridge,
(o)

wherein $R^9$ and m are as defined above,
(p)

wherein $R^9$ and m are as defined above, and
(q) —$R^{11}$;

or any two of X, Y and Z may be joined to form a saturated ring having 5, 6, or 7 ring atoms, said ring atoms comprising 1 or 2 oxygen atoms, the remaining ring atoms being carbon, such as dioxolanyl or dioxanyl;

X′, Y′ and Z′ independently are selected from:
(a) hydrogen,
(b) $C_{1-7}$alkyl,
(c) $C_{2-6}$alkenyl,
(d) halogen,
(e) —$(CH_2)_m$—$NR^6R^7$, wherein $R^6$, $R^7$, and m are as defined above,
(f) —CN,
(g) —CHO,
(h) —$CF_3$,
(i) —$SR^8$, wherein $R^8$ is hydrogen, $C_{1-6}$alkyl, trifluoromethyl, or phenyl,
(j) —$SOR^8$, wherein $R^8$ is as defined above,
(k) —$SO_2R^8$, wherein $R^8$ is as defined above,
(l) —$CONR^6R^7$, wherein $R^6$ and $R^7$ are as defined above,
(m) $R^9O(CH_2)_m$— wherein $R^9$ and m are as defined above,
(n) —$CH(OR^{12})(OR^{13})$, wherein $R^{12}$ and $R^{13}$ are as defined above,
(o)

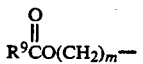

wherein $R^9$ and m are as defined above,
(p)

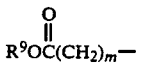

wherein $R^9$ and m are as defined above, and
(q) —$R^{11}$.

The compounds of the present invention have asymmetric centers and this invention includes all of the optical isomers and mixtures thereof.

In addition compounds with carbon-carbon double bonds may occur in Z- and E- forms with all isomeric forms of the compounds being included in the present invention.

When any variable (e.g., alkyl, aryl, $R^6$, $R^7$, $R^8$, $R^9$, $R^{10}$, $R^{11}$, X, Y, Z, etc.) occurs more than one time in any variable or in Formula I, its definition on each occurrence is independent of its definition at every other occurrence.

As used herein, the term "alkyl" includes those alkyl groups of a designated number of carbon atoms of either a straight, branched, or cyclic configuration. Examples of "alkyl" include methyl, ethyl, propyl, isopropyl, butyl, sec-and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy.

"Alkanoyl" is intended to include those alkylcarbonyl groups of specified number of carbon atoms, which are exemplified by formyl, acetyl, propanoyl and butyryl; "alkanoyloxy" is intended to include those alkylcarbonyl groups of specified number of carbon atoms attached through an oxygen bridge, which are exemplified by formyloxy, acetoxy, propionoyloxy, and butyryloxy. "Alkenyl" is intended to include hydrocarbon chains of a specified number of carbon atoms of either a straight- or branched-configuration and at least one unsaturation, which may occur at any point along the chain, such as ethenyl, propenyl, butenyl, pentenyl, dimethyl pentenyl, and the like, and includes E and Z forms, where applicable; and "arylalkyl" represents aryl groups as herein defined which are attached through a straight or branched chain alkyl group of from one to six carbon atoms, such as, for example, benzyl, phenethyl, 3,3-diphenylpropyl, and the like. "Halogen" or "halo", as used herein, means fluoro, chloro, bromo and iodo.

As will be understood by those skilled in the art, pharmaceutically acceptable salts include, but are not limited to salts with inorganic acids such as hydrochloride, sulfate, phosphate, diphosphate, hydrobromide, and nitrate or salts with an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium potassium calcium aluminum, lithium and ammonium (especially ammonium salts with amines of the formula $HNR^6R^7$).

The heteroaryl group as used herein includes acridine, carbazole, cinnoline, dibenzofuran, dibenzothiophene, quinoxaline, pyrrazole, indole, benzotriazole, furan, benzofuran, quinoline, isoquinoline, pyrazie, pyridazine, pyridine, pyrimidine, pyrrole which are optionally substituted.

In the compounds of Formula I the heteroaryl group may be optionally substituted with X, Y and Z at any available carbon atom or nitrogen atom (if present), but compounds bearing certain of X, Y and Z directly substituted to a nitrogen atom of the heteroaryl ring may be relatively unstable and are not preferred.

The term "heteroaryl" as utilized herein is intended to include the following heteraromatic groups which may include X, Y and Z substitution as indicated and wherein Q is —N(X)—, —O—, —S—, —SO—, or —SO$_2$—:

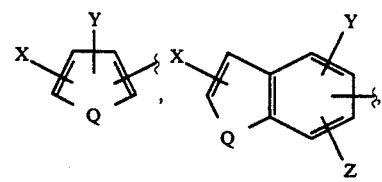

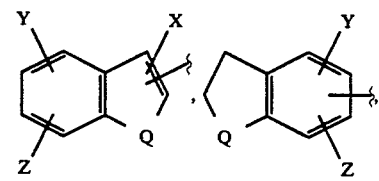

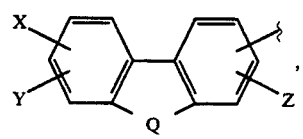

(Pyridine)   (Pyridazine)

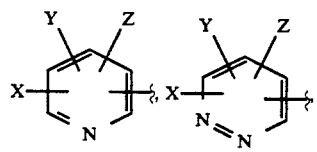

(Pyrimidine)   (Pyrazine)

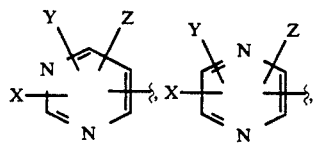

(Quinoline)

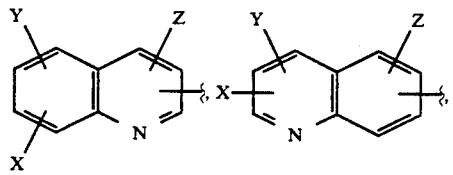

(Isoquinoline)

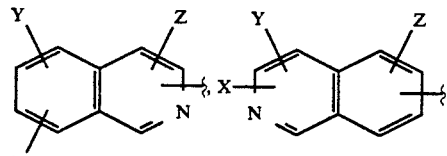

(Cinnoline)

-continued

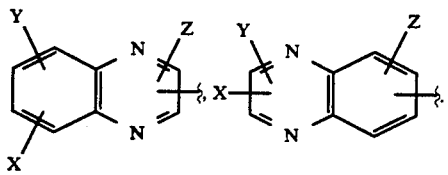

(Quinoxaline)

The aryl or aromatic group may include phenyl or naphthyl which are optionally substituted by from one- to three-members independently selected from the group consisting of: alkyl, alkenyl, halogen, carboxyl, CHO, amino, mono-alkylamino, di-alkylamino, aminoalkyl, mono-alkylaminoalkyl, di-alkylaminoalkyl, alkylthio, alkylsulfinyl, alkylsulfonyl, trifluoromethyl, amido, mono-alkylamido, dialkylamido, hydroxy, hydroxyalkyl, $R^{11}$O-alkyl, alkoxy, alkoxyalkyl, formamido, alkyl-$CO_2$-, formamidoalkyl, alkyl-$CO_2$-alkyl-, carbonxyl, alkyl-$CO_2$H, alkyl-$O_2$C—, alkyl-$O_2$C-alkyl-, and $OR^{11}$.

In the compound of formula I it is preferred that heteroaryl is selected from the group consisting of:

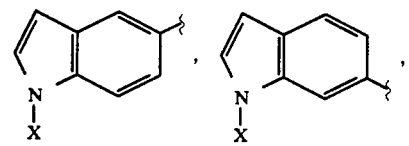

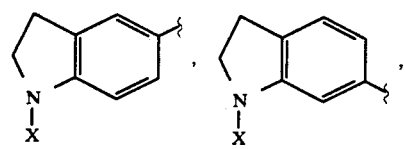

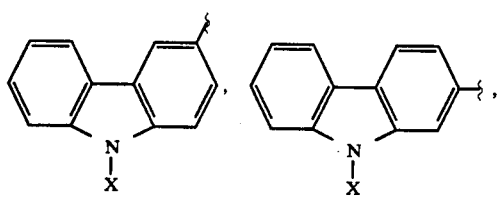

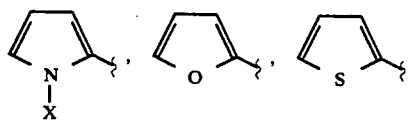

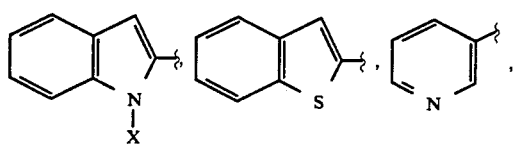

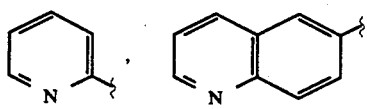

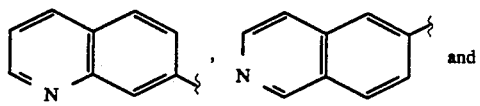 and

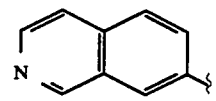

wherein X is as defined above.

In the compound of formula I it is preferred that:

$R^2$ is selected from:
(1) hydrogen,
(2) methyl,
(3) ethyl,
(4) propyl,
(5) allyl,
(6) $R^{11}$,
(7) —$C_{2-3}$alkyl-OH; and
(8) —$C_{2-3}$alkyl-$OR^{11}$;

$R^3$ is selected from:
(1) hydrogen,
(2) hydroxy,
(3) —$OR^{11}$, or $R^3$ and $R^4$ taken together form a double bond;

$R^{10}$ is hydrogen, hydroxy, fluoro, or —$OR^{11}$;

W is 0; and n is 2.

In one embodiment of the present invention, heteroaryl is indole, which may be represented by:

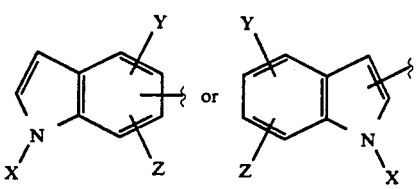

wherein X, Y and Z are as defined above,

Preferred compounds of the present invention include the compounds identified as follows: 42(1-hydroxyethyl-indol-5-yl)oxy-rapamycin.

Representative compounds of the present invention include the compounds of Formula X, XI, XII and XIII:

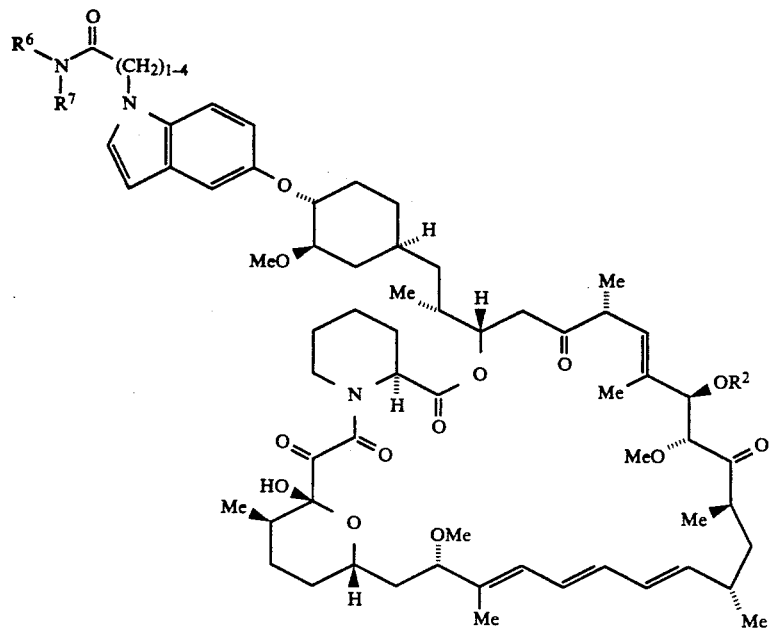
X
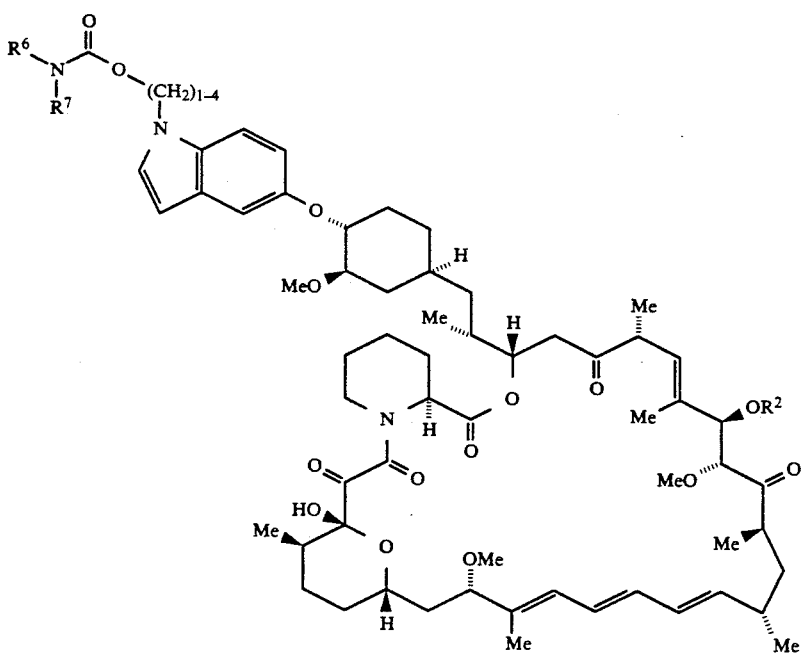
XI

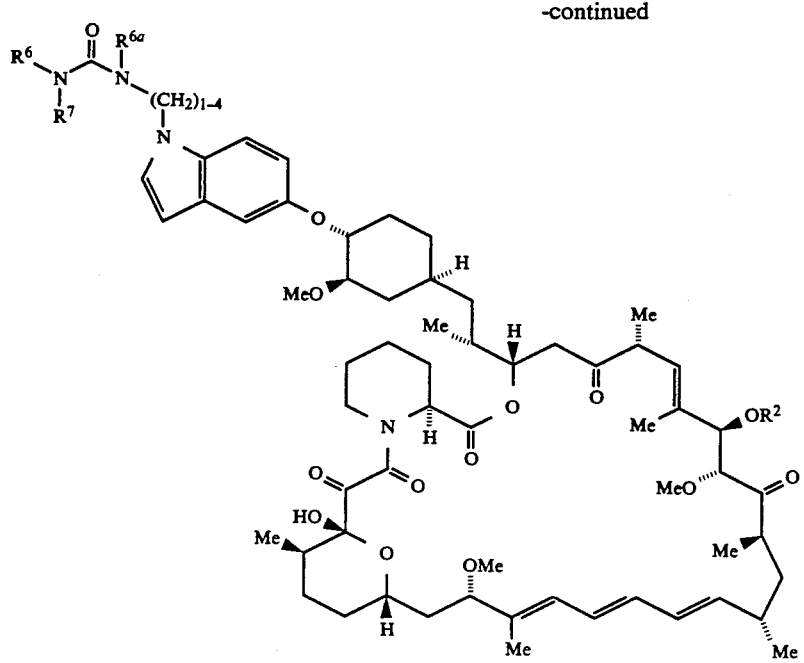

XII

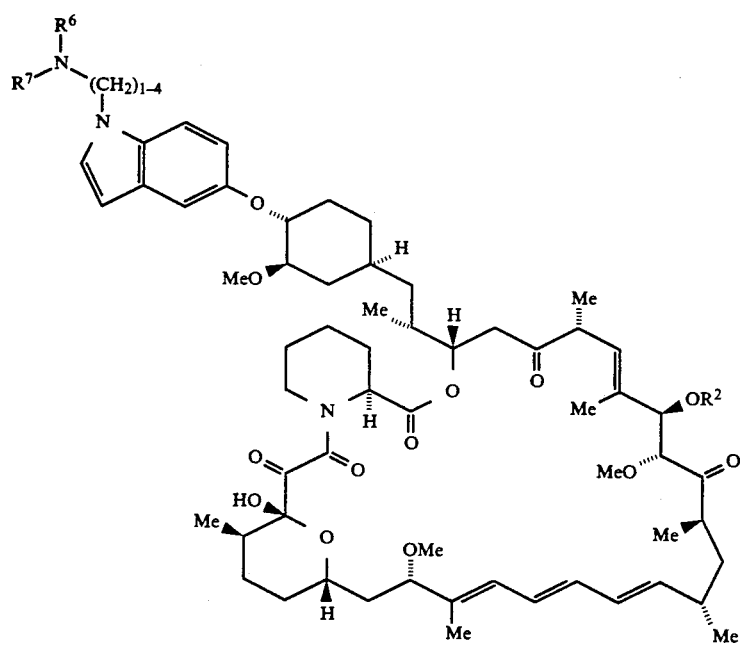

XIII wherein $R^{6a}$ is H or $CH_3$ and the definitions of $R^2$, $R^6$ and $R^7$ are selected from the following groups of substituents:

| $R^6$ | $R^7$ | $R^2$ |
|---|---|---|
| phenyl | phenyl | H |
| phenyl | H | H |
| benzyl | H | H |
| 4-$HO_2C$-benzyl | H | H |
| 4-$H_2NCO$-benzyl | H | H |
| 4-$CH_3O$-benzyl | H | H |
| 4-HO-benzyl | H | H |
| 4-Cl-benzyl | H | H |
| 4-$(CH_3)_2N$-benzyl | H | H |
| 3-$HO_2C$-benzyl | H | H |
| 3-$H_2NCO$-benzyl | H | H |
| 3-$CH_3O$-benzyl | H | H |
| 3-HO-benzyl | H | H |
| 3-Cl-benzyl | H | H |
| 3-$(CH_3)_2N$-benzyl | H | H |
| 4-pyridyl | H | H |
| 3-pyridyl | H | H |
| 2-pyridyl | H | H |
| 4-pyridylmethyl | H | H |
| 3-pyridylmethyl | H | H |
| 2-pyridylmethyl | H | H |
| $CH_3$ | H | H |
| $CH_3CH_2$ | H | H |
| $CH_3CH_2CH_2$ | H | H |
| $(CH_3)_2CH$ | H | H |
| $HO_2CCH_2CH_2$ | H | H |
| $H_2NCOCH_2CH_2$ | H | H |
| $HOCH_2CH_2$ | H | H |
| $HOCH_2CH_2CH_2$ | H | H |
| $CH_3$ | $CH_3$ | H |

17
-continued
| R⁶ | R⁷ | R² |
|---|---|---|
| CH₃CH₂ | CH₃CH₂ | H |
| CH₃CH₂CH₂ | CH₃CH₂CH₂ | H |
| HOCH₂ | HOCH₂ | H |
| HOCH₂CH₂ | HOCH₂CH₂ | H |
| —CH₂CH₂CH₂CH₂CH₂— | | H |
| —CH₂CH₂OCH₂CH₂— | | H |
18
-continued
| R⁶ | R⁷ | R² |
|---|---|---|
| —CH₂CH₂CH₂CH₂— | | H |
Representative compounds of the present invention include the compounds of formula XIV, XV, XVI and XVII:
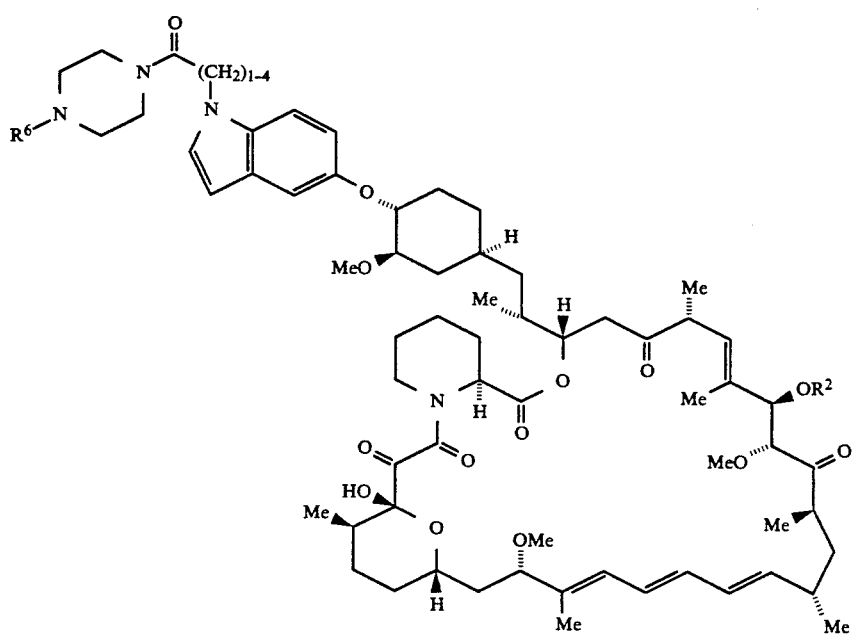
XIV
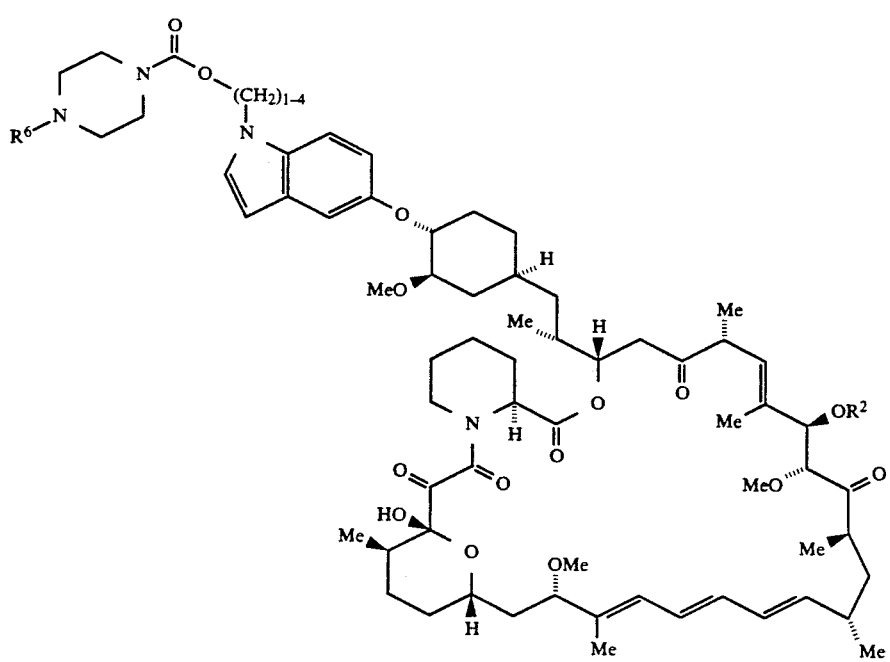
XV

XVI

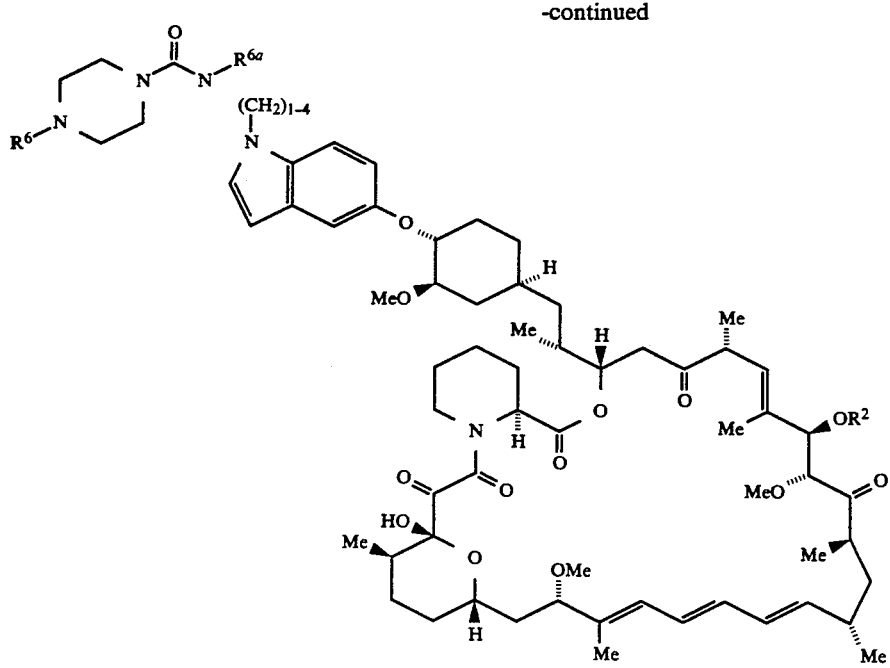

XVII

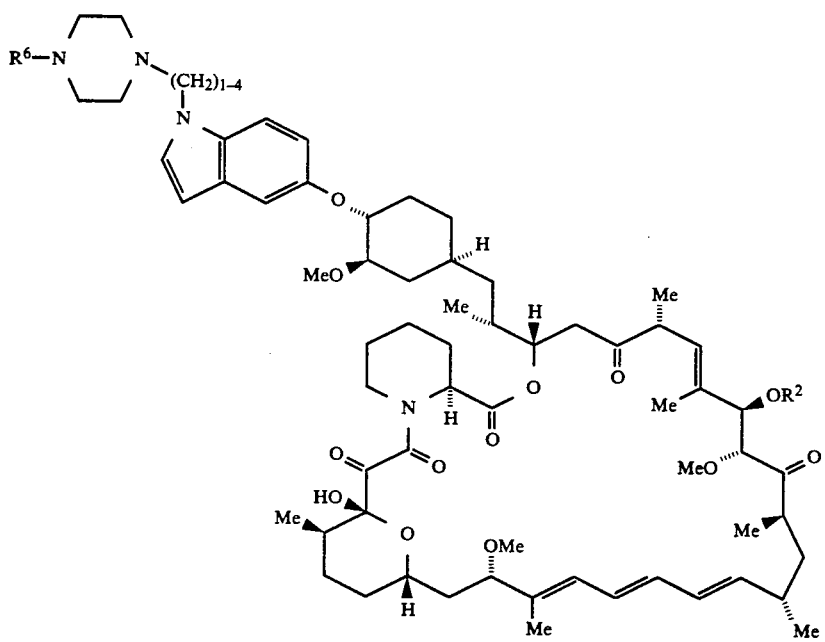

wherein $R^{6a}$ is H or $CH_3$ and $R^2$, and $R^6$ are selected from the following groups of substituents:

| $R^6$ | $R^2$ |
|---|---|
| H | H |
| $CH_3$ | H |
| $CH_3CH_2$ | H |
| $CH_2=CHCH_2$ | H |
| $CH_3CH_2CH_2$ | H |
| $(CH_3)_2CH$ | H |
| $HO_2CCH_2CH_2$ | H |
| $H_2NCOCH_2CH_2$ | H |
| $HOCH_2CH_2$ | H |
| $HOCH_2CH_2CH_2$ | H |
| $(CH_3)_2CH_2$ | H |
| phenyl | H |
| 4-pyridyl | H |
| 3-pyridyl | H |

-continued

| $R^6$ | $R^2$ |
|---|---|
| 2-pyridyl | H |
| 4-pyridylmethyl | H |
| 3-pyridylmethyl | H |
| 2-pyridylmethyl | H |
| benzyl | H |
| 4-$HO_2C$-benzyl | H |
| 4-$H_2NCO$-benzyl | H |
| 4-$CH_3O$-benzyl | H |
| 4-HO-benzyl | H |
| 4-Cl-benzyl | H |
| 4-$(CH_3)_2N$-benzyl | H |
| 3-$HO_2C$-benzyl | H |
| 3-$H_2NCO$-benzyl | H |
| 3-$CH_3$-benzyl | H |
| 3-HO-benzyl | H |
| 3-Cl-benzyl | H |

21
-continued
| R⁶ | R² |
|---|---|
| 3-(CH₃)₂N-benzyl | H |
| 2-HO-benzyl | H |
| 2-Cl-benzyl | H |
22
-continued
| R⁶ | R² |
|---|---|
| 2-(CH₃)₂N-benzyl | H |
Representative compounds of the present invention include the compounds of Formula XVIII, XIX, XX and XXI:
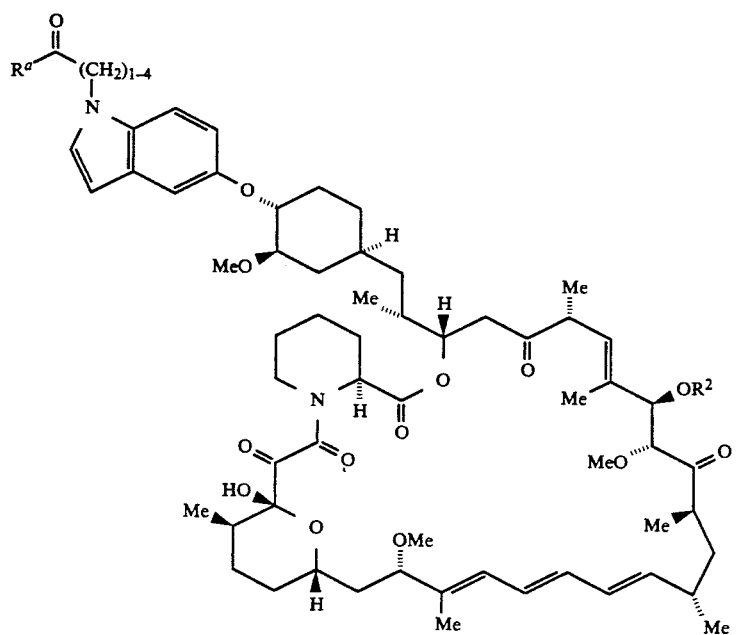
XVIII
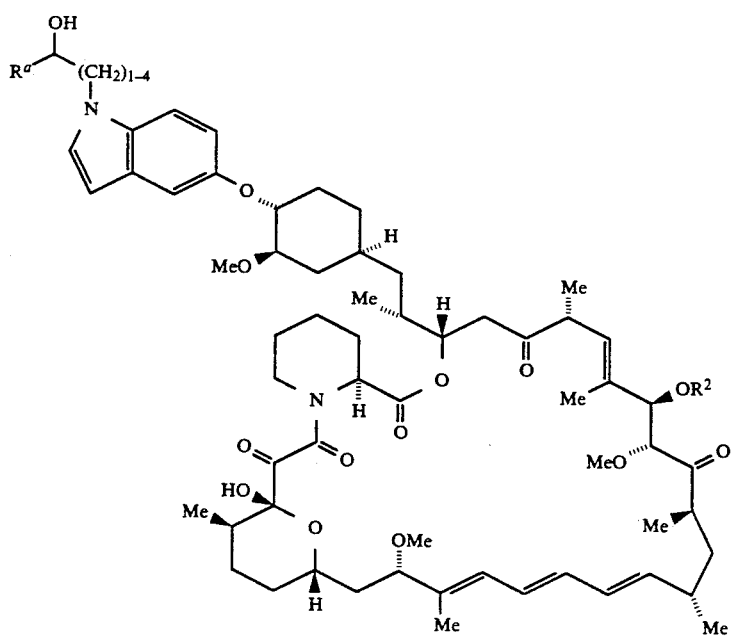
XIX

XX

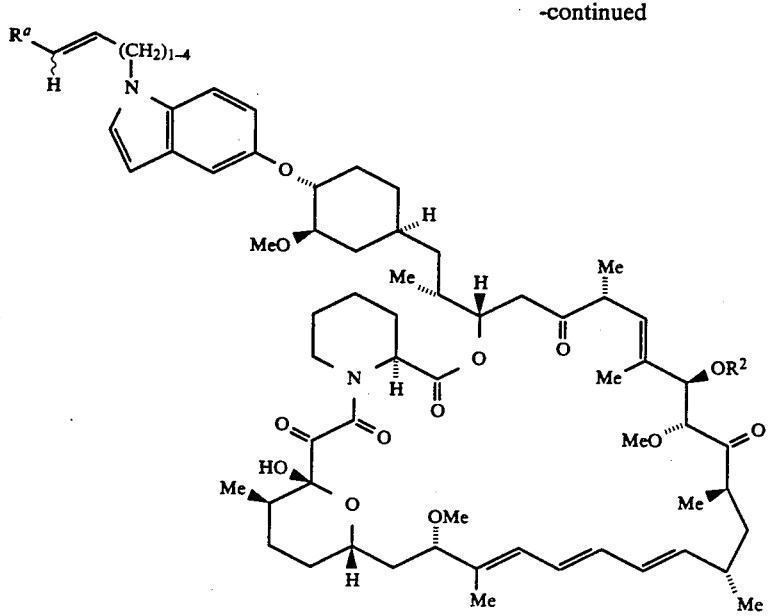

XXI

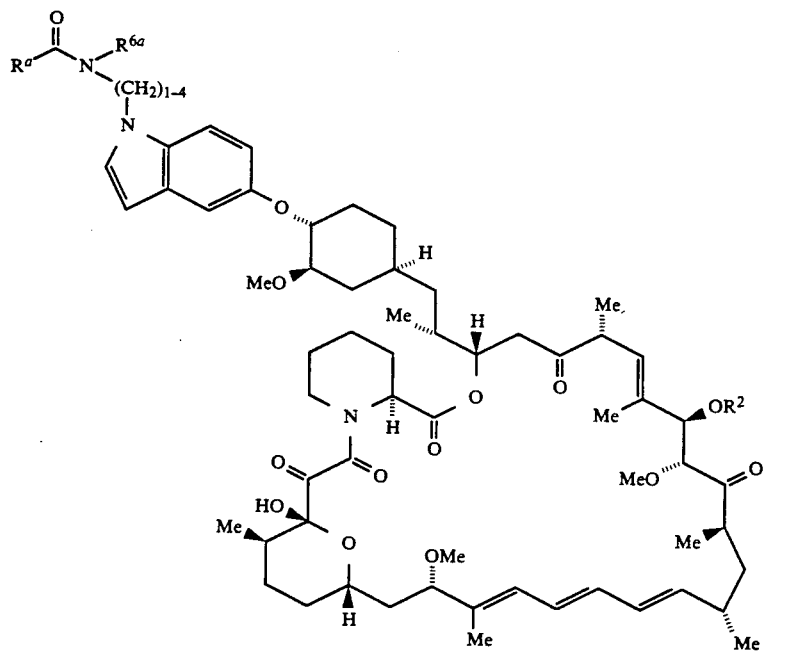

wherein $R^{6a}$ is H or $CH_3$ and $R^a$, $R^2$ and are selected from the following groups of substituents:

| $R^a$ | $R^2$ |
|---|---|
| $CH_3$ | H |
| $CH_3CH_2$ | H |
| $CH_2=CHCH_2$ | H |
| $CH_3CH_2CH_2$ | H |
| $(CH_3)_2CH$ | H |
| $HO_2CCH_2CH_2$ | H |
| $H_2NCOCH_2CH_2$ | H |
| $HOCH_2CH_2$ | H |
| $HOCH_2CH_2CH_2$ | H |
| $(CH_3)_2CH_2$ | H |
| phenyl | H |
| 4-pyridyl | H |
| 3-pyridyl | H |
| 2-pyridyl | H |
| 4-pyridylmethyl | H |
| 3-pyridylmethyl | H |

-continued

| $R^a$ | $R^2$ |
|---|---|
| 2-pyridylmethyl | H |
| benzyl | H |
| 4-$HO_2C$-benzyl | H |
| 4-$H_2NCO$-benzyl | H |
| 4-$CH_3O$-benzyl | H |
| 4-HO-benzyl | H |
| 4-Cl-benzyl | H |
| 4-$(CH_3)_2N$-benzyl | H |
| 3-$HO_2C$-benzyl | H |
| 3-$H_2NCO$-benzyl | H |
| 3-$CH_3O$-benzyl | H |
| 3-HO-benzyl | H |
| 3-Cl-benzyl | H |
| 3-$(CH_3)_2N$-benzyl | H |
| 2-$HO_2C$-benzyl | H |
| 2-$H_2NCO$-benzyl | H |
| 2-$CH_3O$-benzyl | H |
| 2-HO-benzyl | H |
| 2-Cl-benzyl | H |

| -continued | |
|---|---|
| $R^a$ | $R^2$ |
| 2-(CH$_3$)$_2$N-benzyl | H |

Representative compounds of the present invention include the compounds of Formula XVIII:

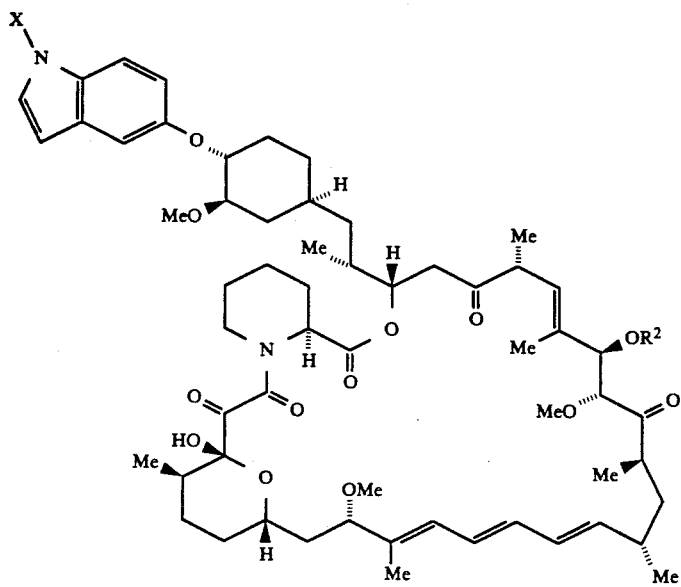

XVIII wherein X and R$^2$ are selected from the following groups of substituents:

| X | R$^2$ |
|---|---|
| 1-imidazolylmethyl | H |
| 2-imidazolylmethyl | H |
| 3-thiazolylmethyl | H |
| 2-thiazolylmethyl | H |
| 2-oxazolylmethyl | H |
| 5-tetrazolylmethyl | H |
| 4-pyridylmethyl | H |
| 3-pyridylmethyl | H |
| 2-pyridylmethyl | H |
| benzyl | H |
| 4-HO$_2$C-benzyl | H |
| 4-H$_2$NCO-benzyl | H |
| 4-CH$_3$O-benzyl | H |
| 4-HO-benzyl | H |
| 4-R$^{11}$O-benzyl | H |
| 4-Cl-benzyl | H |
| 4-(CH$_3$)$_2$N-benzyl | H |
| 3-HO$_2$C-benzyl | H |
| 3-H$_2$NCO-benzyl | H |
| 3-CH$_3$O-benzyl | H |
| 3-HO-benzyl | H |
| 3-R$^{11}$O-benzyl | H |
| 3-Cl-benzyl | H |
| 3-(CH$_3$)$_2$N-benzyl | H |
| 2-HO$_2$C-benzyl | H |
| 2-H$_2$NCO-benzyl | H |
| 2-CH$_3$O-benzyl | H |
| 2-HO-benzyl | H |
| 2-R$^{11}$O-benzyl | H |
| 2-Cl-benzyl | H |
| 2-(CH$_3$)$_2$N-benzyl | H |
| 3-(4-pyridyl)-imidazol-2-ylmethyl | H |
| 3-(3-pyridyl)-imidazol-2-ylmethyl | H |
| 3-(2-pyridyl)-imidazol-2-ylmethyl | H |
| 3-phenylimidazol-2-ylmethyl | H |
| 3-(4-HO$_2$C-phenyl)-imidazol-2-ylmethyl | H |
| 3-(4-H$_2$NCO-phenyl)-imidazol-2-ylmethyl | H |
| 3-(4-CH$_3$O-phenyl)-imidazol-2-ylmethyl | H |
| 3-(4-HO-phenyl)-imidazol-2-ylmethyl | H |
| 3-(4-R$^{11}$O-phenyl)-imidazol-2-ylmethyl | H |
| 3-(4-Cl-phenyl)-imidazol-2-ylmethyl | H |
| 3-(4-(CH$_3$)$_2$N-phenyl)-imidazol-2-ylmethyl | H |
| 3-(3-HO$_2$C-phenyl)-imidazol-2-ylmethyl | H |
| 3-(3-H$_2$NCO-phenyl)-imidazol-2-ylmethyl | H |
| 3-(3-CH$_3$O-phenyl)-imidazol-2-ylmethyl | H |
| 3-(3-HO-phenyl)-imidazol-2-ylmethyl | H |
| 3-(3-R$^{11}$O-phenyl)-imidazol-2-ylmethyl | H |
| 3-(3-Cl-phenyl)-imidazol-2-ylmethyl | H |
| 3-(3-(CH$_3$)$_2$N-phenyl)-imidazol-2-ylmethyl | H |
| 3-(2-HO$_2$C-phenyl)-imidazol-2-ylmethyl | H |
| 3-(2-H$_2$NCO-phenyl)-imidazol-2-ylmethyl | H |
| 3-(2-CH$_3$O-phenyl)-imidazol-2-ylmethyl | H |
| 3-(2-HO-phenyl)-imidazol-2-ylmethyl | H |
| 3-(2-R$^{11}$O-phenyl)-imidazol-2-ylmethyl | H |
| 3-(2-Cl-phenyl)-imidazol-2-ylmethyl | H |
| 3-(2-(CH$_3$)$_2$N-phenyl)-imidazol-2-ylmethyl | H |

B. Preparation of Compounds Within the Scope of the Present Invention

A starting material for the preparation of the compounds of this invention is rapamycin:

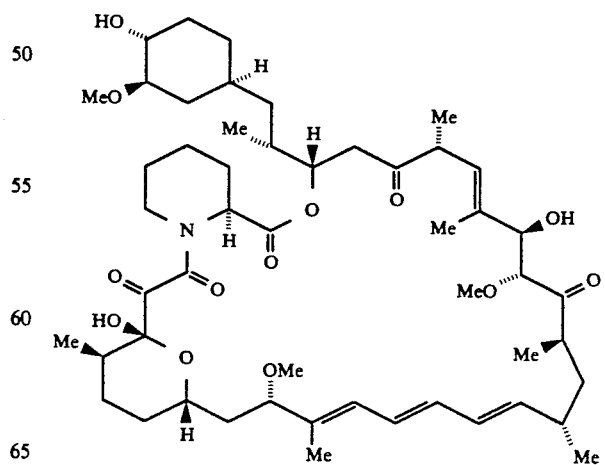

The production and characterization of rapamycin is well known in the literature (see U.S. Pat. No. 3,929,992 issued Dec. 30, 1975; U.S. Pat. No. 3,993,749 issued Nov. 23, 1976). Analogs of rapamycin, such as 30-desmethylrapamycin (see PCT Patent Publication WO 92/14737) or 29-hydroxy rapamycin (see U.S. Pat. No. 5,138,051) may also be employed as starting material to give analagous derivatives. The novel processes for preparing the novel compounds of the present invention are illustrated as follows, wherein $R^1$ and $R^2$ are as defined above unless otherwise indicated. It will be readily apparent to one of ordinary skill in the art reviewing the synthetic route depicted below that other compounds within Formula I can be synthesized by substitution of appropriate reactants and agents int eh synthesis shown below.

REACTION SCHEME B

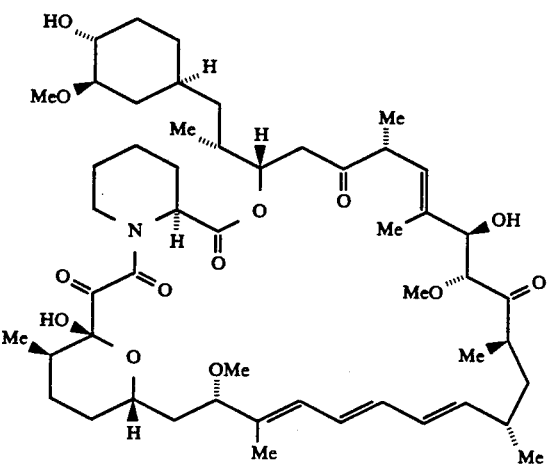

REACTION SCHEME A

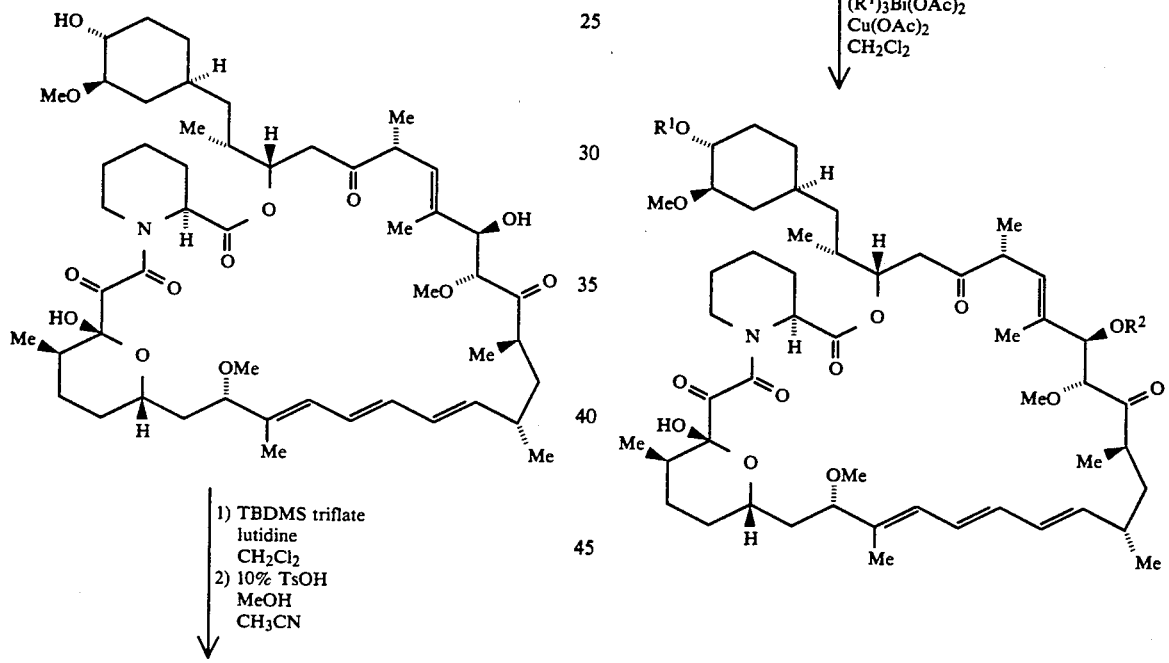

REACTION SCHEME C

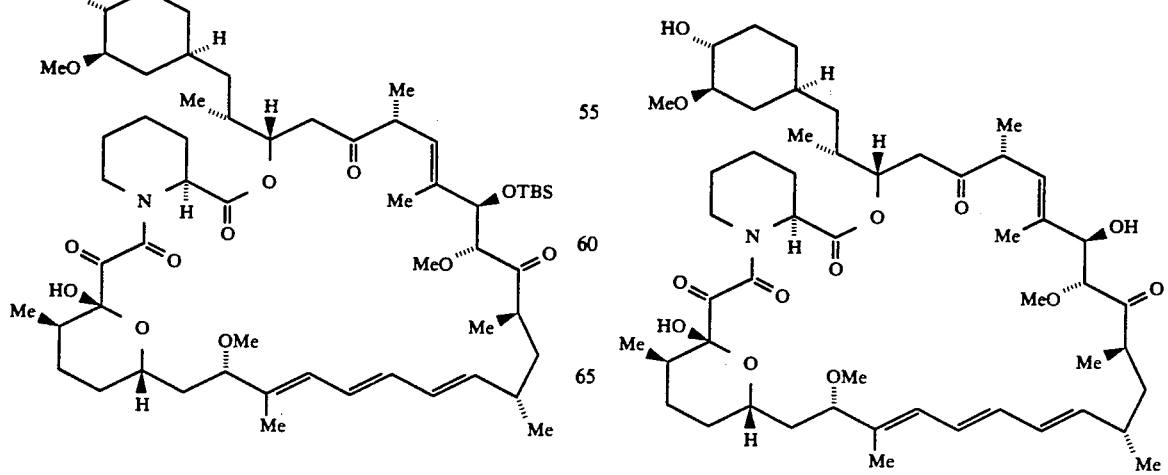

-continued
REACTION SCHEME C
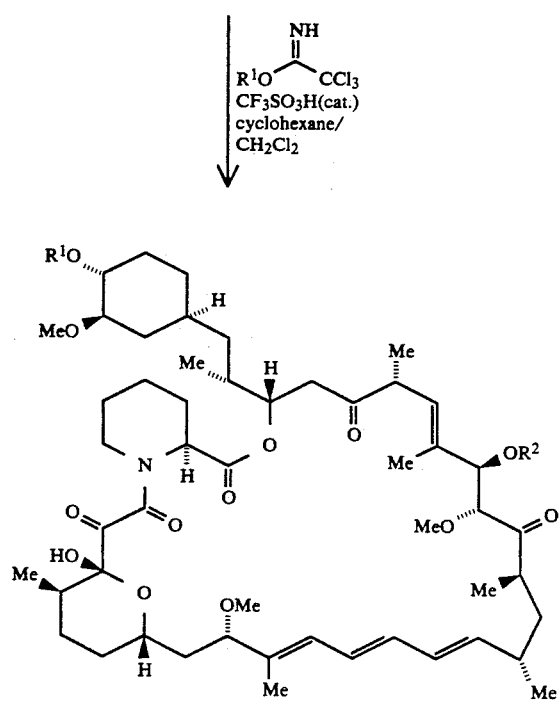
REACTION SCHEME E
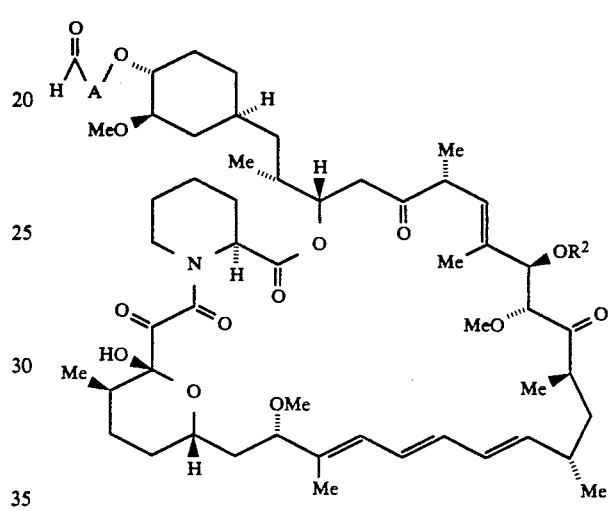
REACTION SCHEME E
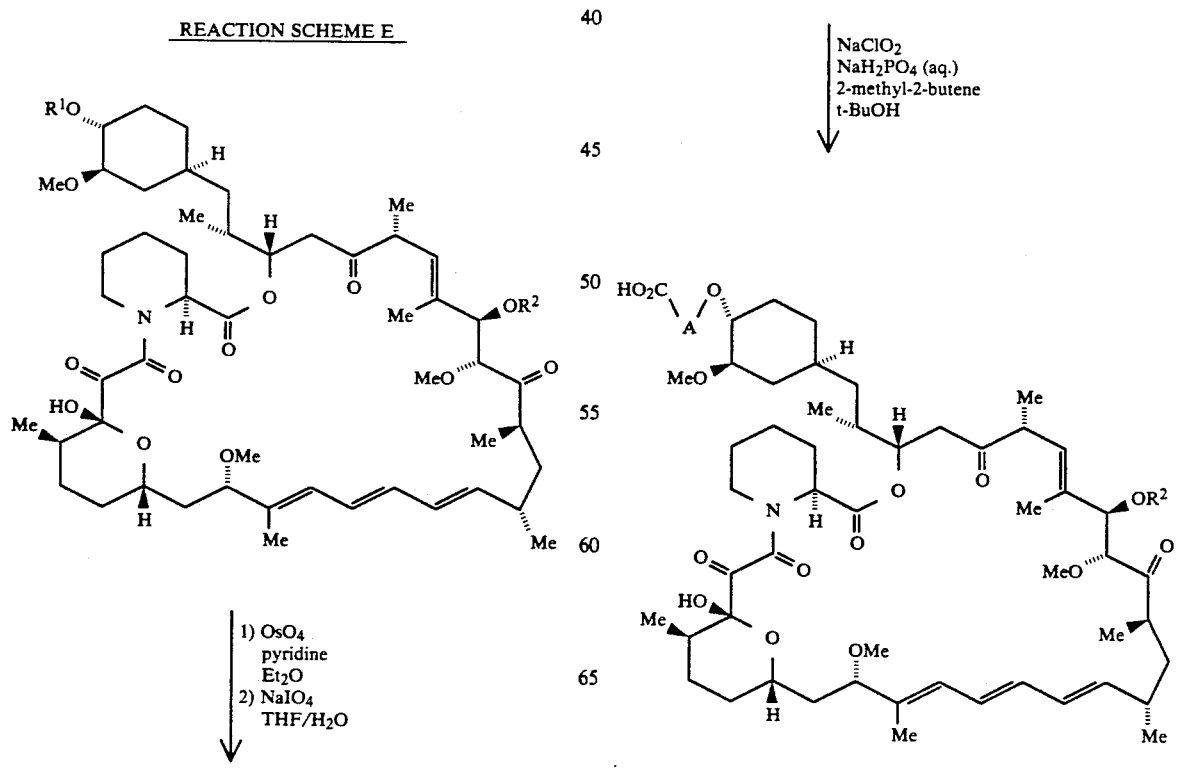

REACTION SCHEME F
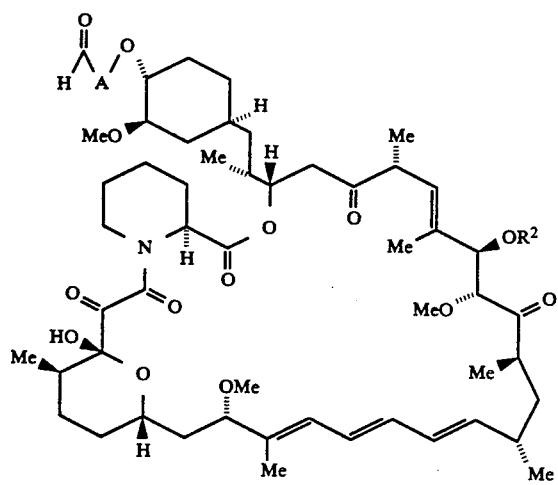
↓ R⁶R⁷NH  NaCNBH₃  THF
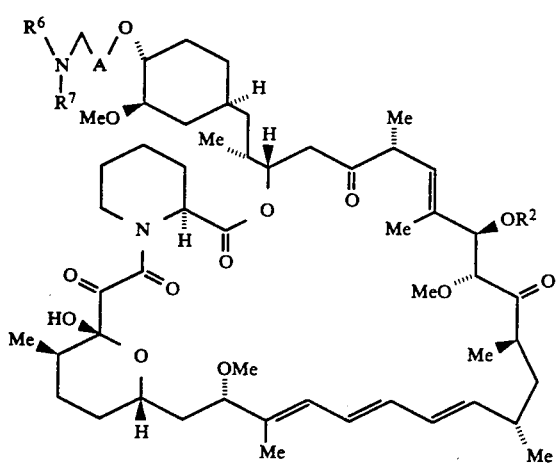
↓ K(Ph)₃BH  THF
-continued
REACTION SCHEME F
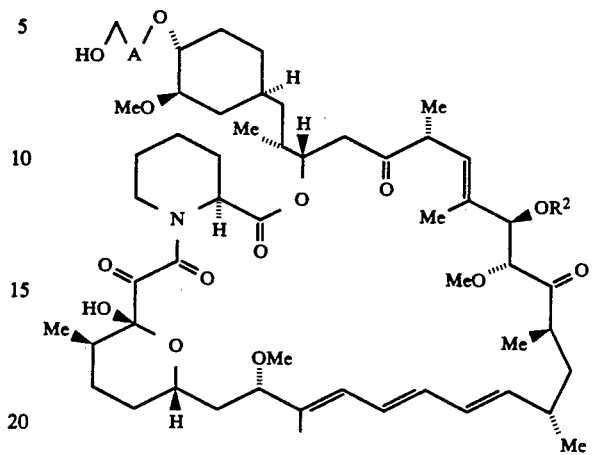
REACTION SCHEME G
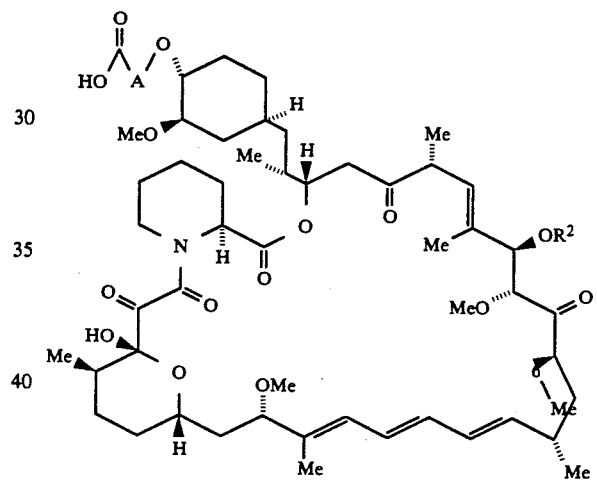
↓ R⁶R⁷NH  HOBt  EDC  CH₂Cl₂/DMF
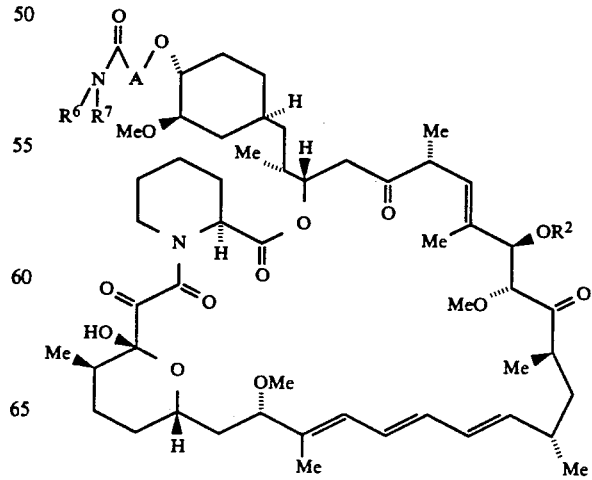

REACTION SCHEME H

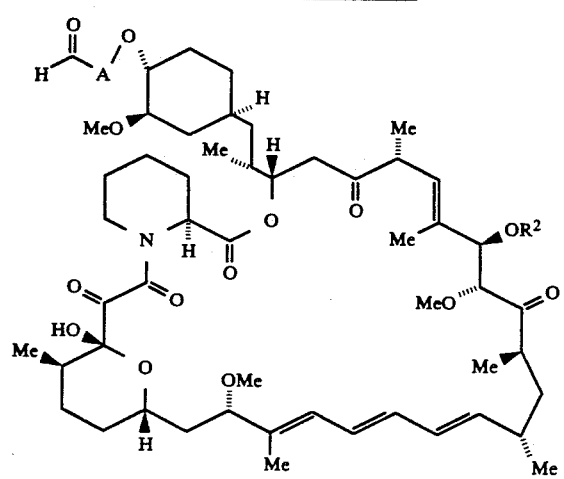

R$^{1a}$MgBr
THF
−78° C.

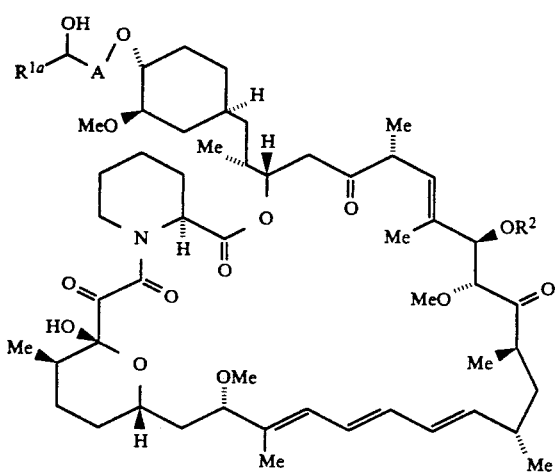

TPAP (cat.)
NMO
4A sieves
CH$_2$Cl$_2$

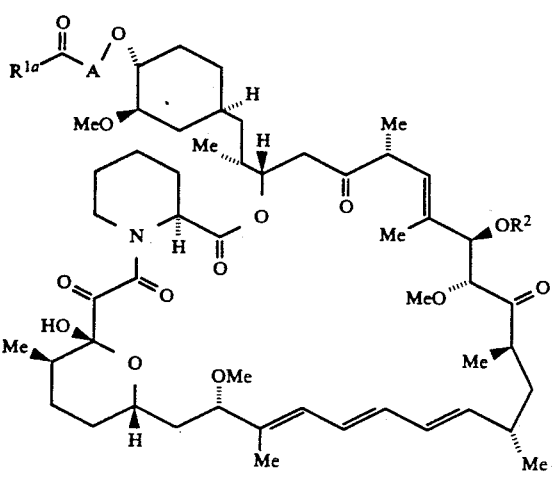

REACTION SCHEME I

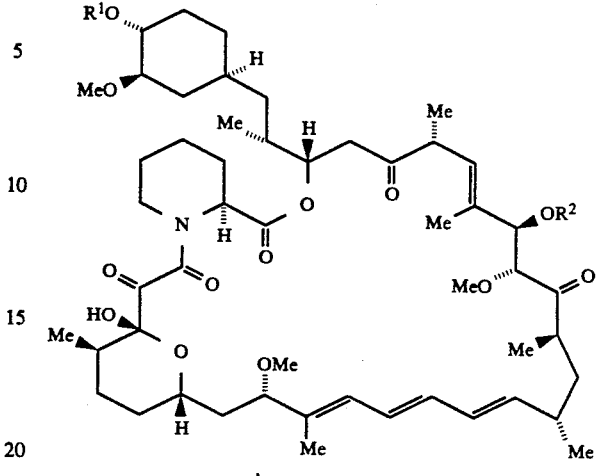

Acylation
or
Phosphorylation

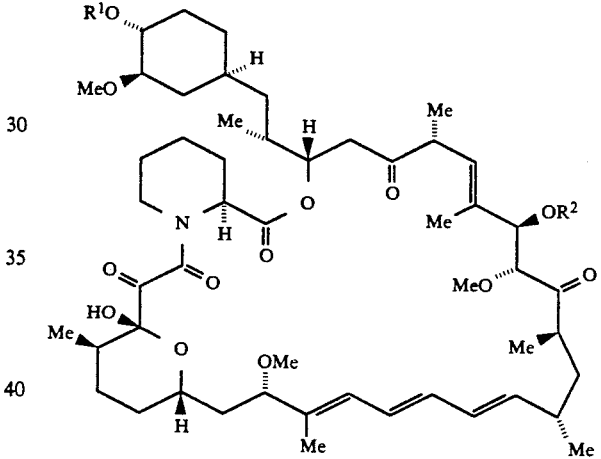

Reaction Scheme A:

Protection of the C-31 and/or the C-42 hydroxy group may be accomplished by methods known in the prior art for rapamycin (see e.g. U.S. Pat. No. 5,120,842) such as by treatment with: 2,6-lutidine and triisopropylsilyl trifluoromethanesulfonate in a solution of methylene chloride; 2,6-lutidine and t-butyldimethylsilyl trifluoromethanesulfonate in a solution of methylene chloride; pyridine and acetic anhydride in a solution of methylene chloride; pyridine and benzoyl chloride in a solution of methylene chloride; pyridine and p-nitrobenzoyl chloride in a solution of methylene chloride; imidazole and t-butyldiphenylsilyl chloride in a solution of methylene chloride; and the like. For example, as shown in Reaction Scheme A, rapamycin may be protected at C-42 as the t-butyldimethylsilyl ether by treatment with one equivalent of t-butyldimethylsilyl trifluoromethanesulfonate in methylene chloride to give the C-42-di-O-TBMS triflate followed by treatment with acetic acid or toluene-sulfonic acid in methanol results in selective removal of the C-42 ether to give the C-31-O-TBDMS macrolide.

Reaction Scheme B:

As shown in Reaction Scheme B, a solution of rapamycin in an inert organic solvent such as methylene chloride, benzene, toluene, chloroform, or the like or mixtures thereof may be treated with a triarylbismuth diacetate reagent (wherein $R^1$ is aryl) (prepared immediately prior to use by the addition of acetic acid to a suspension of a triarylbismuth carbonate in an inert organic solvent such as methylene chloride, chloroform or the like or mixtures thereof) in the presence of a catalytic amount of copper(II) acetate at a temperature of 20°–50° C., preferably room temperature, for a period of one hour to seven days, preferably one day, to give the 42-O-aryl rapamycin and/or the 31, 42-di-O-aryl rapamycin. Alternatively, the triarylbismuth(V) reagent may be prepared by treatment of a triarylbismuthine with a suitable oxidant such as peracetic acid, iodobenzene diacetate, bis(trifluoroacetoxy)iodobenzene and the like in an inert solvent such as methylene chloride, chloroform, benzene, toluene and the like. The triarylbismuth(V) reagent may be used without purification or may be purified by silica gel chromatography. Triarylbismuthines may be prepared by the reaction of an appropriate aryl Grignard reagent with bismuth trichloride in an inert organic solvent such as tetrahydrofuran, diethyl ether, or 1,4-dioxane, or mixtures thereof, at or near room temperature for a period of 1 to 48 hours. General procedures for the preparation and use of triaryl bismuth reagents may be found in Barton, D. H. E., et al., *J. Chem. Soc. Chem. Commun.*, 1986, 65 and references cited therein.

Similarly, the 31-O-aryl compounds may be prepared by protecting the 42-alcohol or rapamycin with a protecting group, such as with a tert-butyl dimethylsilyl group, followed by arylation of the 31-position with a triaryl bismuth reagent. Removal of the protecting group provides the 31-O-aryl compounds. In the case of the tert-butyl dimethylsilyl protecting group, deprotection can be accomplished under mildly acidic conditions.

If desired, the 31-hydroxy-42-O-aryl rapamycin, or 31-O-aryl-42-hydroxy rapamycin may be treated with a different triarylbismuth diacetate reagent (prepared immediately prior to use by procedures analogous to those disclosed above), to give mixed 31-O-aryl-42-O-aryl macrolides.

Reaction Scheme C:

As shown in Reaction Scheme C, a solution of the rapamycin in an inert organic solvent such as methylene chloride, chloroform, pentane, hexane, cyclohexane, heptane or the like or mixtures thereof is treated with an alkyl, alkenyl or alkynyl trichloroacetimidate reagent (prepared by the reaction of an appropriate sodium alkoxide with trichloroacetonitrile, such as described by Wessel, H. P., Iversen, T., Bundle, D. R., *J. Chem. Soc., Perkin Trans. I*, 1985, 2247) in the presence of a mild acid catalyst such as trifluoromethanesulfonic acid, p-toluenesulfonic acid, methane-sulfonic acid, enzenesulfonic acid, p-nitrobenzene-sulfonic acid, p-bromobenzenesulfonic acid, p-chlorobenzenesulfonic acid, or p-methoxybenzenesulfonic acid, or mixtures thereof at a temperature of 20°–50° C., preferably room temperature, for a period of one hour to seven days, preferably one day, to give the 31- and/or 42-O-alkyl, -alkenyl or -alkynyl rapamycin derivative.

In addition, the procedure of Reaction Schemes A, B, and C may be combined to produce rapamycin derivatives bearing O-aryl, O-alkyl, O-alkenyl and/or O-alkynyl substituents at the 31 and 42 positions.

The procedures described in Reaction Scheme B may be conducted on the mono-substituted products of Reaction Scheme C (and vice versa) to obtain the mixed disubstituted compounds. In fact, within Reaction Schemes B and C, treatment of the mono-substituted product with a different reagent will afford the mixed disubstituted compounds.

Reaction Scheme E:

As shown in Reaction Scheme E, the 42-hydroxy-31-$R^2$O-macrolide or alternatively the 31-hydroxy-42-$R^1$O-macrolide (not depicted) (wherein $R^3$ is protected hydroxy or hydrogen) may be reacted with an alkenyl trichloroacetimidate (wherein $R^1$ is $C_{3-10}$ alkenyl) under conditions described in Reaction Scheme C to give the C-42-O-alkenyl macrolide. Treatment with a stoichiometric amount of osmium tetraoxide in an inert organic solvent, such as diethyl ether or tetrahydrofuran, in the presence of an amine base, such as pyridine or 4-methylmorpholine N-oxide, at or near room temperature gives the corresponding glycol. Treatment of the glycol with sodium metaperiodate in a solution of tetrahydrofuran/water gives the aldehyde (wherein A is $C_{1-8}$ alkyl). Alternatively, the alkenyl macrolide may be treated with sodium metaperiodate in a presence of a catalytic amount of osmium tetraoxide in an organic solvent to give the aldehyde directly. The aldehyde may be further oxidized to the carboxylic acid by treatment with sodium chlorite in buffered, aqueous tert-butanol.

Reaction Scheme F:

A variety of compounds may be prepared from the corresponding aldehyde as illustrated in Reaction Scheme F. The aldehyde may be reacted with a primary or secondary amine (wherein $R^6$ and $R^7$ are as defined above) in an organic solvent such as tetrahydrofuran to give an imine which is reduced in situ with a hydride reducing agent, such as potassium triphenyl borohydride or sodium cyanoborohydride, to give the macrolide bearing an amino alkoxy functionality at C-42. The aldehyde may also be reduced to the corresponding alcohol by treatment with a hydride reducing agent, such as potassium triphenyl borohydride or sodium cyanoborohydride in an organic solvent such as tetrahydrofuran. The alcohol may be further modified by utilizing the methods of Reaction Scheme B (wherein $R^1$ is unsubstituted or substituted phenyl, naphthyl or biphenyl) or Reaction Scheme F (wherein $R^1$ is unsubstituted or substituted alkyl, alkenyl or alkynyl) to give the corresponding ether. The procedures described in Reaction Scheme F are readily applicable to the preparation of compounds bearing analogous functionality at C-31.

Reaction Scheme G:

Amide derivatives may be prepared from the carboxylic acid as illustrated in Reaction Scheme G. The carboxylic acid may be coupled with a primary or secondary amine, $NHR^6R^7$ (wherein $R^6$ and/or $R^7$ are as defined) by any of the peptide coupling methods commonly used in the art, such as with BOP reagent, DCC/HOBT, or EDC/HOBT.

Reaction Scheme H:

Hydroxy and keto derivatives may be prepared from the corresponding aldehyde as illustrated in Reaction Scheme H. The aldehyde is reacted with a nucleophilic organometallic reagent such as a Grignard reagent, an organolithium reagent, or an orgnaocerium reagent in an organic solvent such as methylene chloride or tetrahydrofuran to give the substituted hydroxy compound. Removal of hydroxy protecting groups at other positions of the macrolide (if necessary) gives the macrolide bearing a substituted hydroxy alkoxy functionality at C-42. The alcohol may also be oxidized to the corresponding ketone by well known methods, such as with 4-methylmorpholine-N-oxide in the presence of tetrapropylammonium perruthenate catalyst under dehydrative conditions. Removal of hydroxy protecting groups (if necessary) gives the macrolide bearing a substituted keto alkoxy functionality at C-42. The procedures described in Reaction Scheme H are readily applicable to the preparation of compounds bearing analogous functionality at C-31.

Reaction Scheme I:

Hydroxy macrolides (wherein $R^1$ and/or $R^2$ bear a hydroxy group) may be further derivatized by alkylation, acylation or phosphorylation to give ether, ester or phosphate derivatives (wherein $R^1$ and/or $R^2$ bear an $-OR^{11}$ as defined above) by procedures well known to the practitioner of the art.

The object compounds of Formula I obtained according to the reactions as explained above can be isolated and purified in a conventional manner, for example, extraction, precipitation, fractional crystallization, recrystallization, chromatography, and the like.

It is to be noted that in the aforementioned reactions and the post-treatment of the reaction mixture therein, the stereoisomer(s) of starting and object compounds due to asymmetric carbon atom(s) or double bond(s) of the object compounds of Formula I may occasionally be transformed into the other stereoisomer(s), and such cases are also included within the scope of the present invention.

In the present invention, compounds with asymmetric centers may occur as racemates, as diastereomeric mixtures and as individual diastereomers, with all isomeric forms of the compounds being included in the present invention.

The compounds of the present invention are capable of forming salts with various inorganic and organic acids and bases and such salts are also within the scope of this invention. Examples of such acid addition salts (which are negative counterions defined herein as $M^-$) include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, oxalate, pamoate, persulfate, picrate, pivalate, propionate, succinate, tartrate, tosylate, and undecanoate. Base salts (which are positive counterions defined herein as $M^+$) include ammonium salts, alkali metal salts such as sodium, lithium and potassium salts, alkaline earth metal salts such as calcium and magnesium salts, salts with organic bases such as dicyclohexylamine salts, N-methyl-D-glucamine, and salts with amino acids such as arginine, lysine and so forth. Also, the basic nitrogen-containing groups may be quaternized with such as agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

C. Utility of the compounds within the scope of the invention

The compounds of Formula I may be employed as immunosuppressants or antimicrobial compounds by methods and in dosages known in the prior art for rapamycin. These compounds possess pharmacological activity such as immunosuppressive activity, antimicrobial activity, and the like, and therefore are useful for the treatment and prevention of the resistance to transplantation or transplantation rejection of organs or tissues such as heart, kidney, liver, duodenum, small-bowel, medulla ossium, skin, pancreatic islet-cell, etc., graft-versus-host diseases by medulla ossium transplantation, autoimmune diseases such as rheumatoid arthritis, systemic lupus erythematosis, Hashimoto's thyroiditis, multiple sclerosis, myasthenia gravis, type I diabetes, uveitis, allergic encephalomyelitis, glomerulonephritis, etc., and infectious diseases caused by pathogenic microorganisms, particularly fungal infections.

The compounds of Formula I are also useful for treating or preventing inflammatory and hyperproliferative skin diseases and cutaneous manifestations of immunologically-mediated illnesses such as: psoriasis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, acne, cutaneous eosinophilias or Alopecia areata. More particularly, the compounds of Formula I are useful in hair revitalizing, such as in the treatment or prevention of male pattern alopecia or alopecia senilis, by providing epilation prevention, hair germination, and/or a promotion of hair generation and hair growth.

The compounds of Formula I are further useful for treating or preventing reversible obstructive airways disease, including conditions such as asthma, including bronchial asthma, allergic asthma, intrinsic asthma, extrinsic asthma and dust asthma, particularly chronic or inveterate asthma (for example late asthma and airway hyper-responsiveness), bronchitis and the like. The compounds of Formula I may also be useful for treating hepatic injury associated with ischemia.

The compounds of Formula I are also useful for treating multidrug resistance of tumor cells, (i.e. enhancing the activity and/or sensitivity of chemotherapeutic agents), preventing or treating inflammation of mucosa or blood vessels, $LTB_4$-mediated diseases, gastric ulcers, vascular damage caused by ischemic diseases and thrombosis, ischemic bowel disease, inflammatory bowel disease (e.g., Crohn's disease and ulcerative colitis) necrotizing enterocolitis, or intestinal lesions associated with thermal burns, cytomegalovirus infection, particularly HCMV infection, idiopathic thrombocytopenic purpura and Basedow's disease.

Further, the compounds of Formula I are also useful for treating or preventing renal diseases selected from interstitial nephritis, Goodpasture's syndrome, hemolytic-uremic syndrome and diabetic nephropathy; nervous diseases selected from multiple myositis, Guillain-Barre syndrome, Meniere's disease and radiculopathy; endocrine diseases selected from hyperthyroidism; hematic diseases selected from pure red cell aplasia, aplastic anemia, hypoplastic anemia, autoimmune hemolytic anemia, agranulocytosis and anerythroplasia; bone diseases such as osteoporosis; respiratory diseases selected from sarcoidosis, fibroid lung and idiopathic interstitial pneumonia; eye diseases selected from herpetic keratitis, conical cornea, dystrophia epithelialis corneae, corneal leukmas, ocular pemphigus, Mooren's ulcer, scleritis and Grave's ophthalmopathy; skin diseases selected from dermatomyositis, leukoderma vulgaris, ichthyosis vulgaris, photoallergic sensitivity and cutaneous T cell lymphoma; circulatory diseases selected from arteriosclerosis, aortitus syndrome, polyarteritis nodosa and myocardosis; collagen diseases selected from scleroderma, Wegener's granuloma and Sjogren's syndrome; adiposis; eosinophilic fasciitis; periodontal disease; and muscular dystrophy.

The compounds of Formula I are useful for the treatment of fungal infections in animals, especially mammals, including humans, in particular humans and domesticated animals (including farm animals). The compounds may be used for the treatment of topical fungal infections in man caused by, among other organisms, species of Candida, Trichophyton, Microsporum or Epidermophyton or in mucosal infections caused by *Candida Albicans* (e.g. thrush and vaginal candidiasis). They may also be used in the treatment of systemic fungal infections caused by, for example *Candida albicans, Cryptococcus neoformans, Aspergillus fumigatus,* Coccidiodes, Paracocciciodes, Histoplasma or Blastomyces spp. They may also be of use in treating eumycotic mycetoma, chromoblastomycosis and phycomycosis.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual nontoxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of diseases.

For the treatment of these conditions and diseases caused by immunoirregularity a compound of formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

Dosage levels of the compounds of the present invention are of the order from about 0.005 mg to about 50 mg per kilogram of body weight per day, preferably from about 0.1 mg to about 10 mg per kilogram of body weight per day, are useful in the treatment of the above-indicated conditions (from about 0.7 mg to about 3.5 g per patient per day, assuming a 70 kg patient). In addition, the compounds of the present invention may be administered on an intermittent basis; i.e. at daily, semi-weekly, weekly, semi-monthly or monthly intervals.

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain from about 0.5 mg to about 500 mg of active ingredient, and preferably about 0.5 mg to about 100 mg of active ingredient. For external administration the compound of Formula I may be formulated within the range of, for example, 0.0001% to 60% by weight, preferably from 0.001 to 10% by weight, and most preferably from about 0.005 to 0.8% by weight.

It will be understood, however, that the specific dose level for any particular patient will depend on a variety of factors including the activity of the specific compound employed, the age, body weight, general health, sex, diet, time of administration, route of administration, rate of excretion, drug combination and the severity of the particular disease undergoing therapy.

The following examples are given for the purpose of illustrating the present invention and shall not be construed as being limitations on the scope or spirit of the instant invention.

EXAMPLE A

General procedure for the preparation of triarylbismuthines

To a stirred suspension of magnesium (486 mg, 20 mmol) in dry tetrahydrofuran (10 mL) is added slowly a solution of aryl halide (20 mmol) in dry tetrahydrofuran (10 mL). If necessary the mixture is warmed gently to effect Grignard formation. To the stirred solution of the Grignard reagent is added a solution of bismuth trichloride (1.9 g, 6 mmol) dissolved in dry tetrahydrofuran (20 mL). The resulting mixture is stirred for 24 hours. The reaction mixture is poured into a separatory funnel containing brine and extracted 4x with $CH_2Cl_2$. The organic extracts were combined and dried over anhydrous $Na_2SO_4$. The mixture was filtered and concentrated in vacuo. The triarylbismuthine is isolated and purified by flash column chromatography on silica gel.

EXAMPLE 1

42-(1-N-Methyl-5-indolyl)oxy-rapamycin

STEP 1A

1-Methyl-5-bromoindole

A mixture of sodium hydroxide (0.4 g., 10 mmol.) in DMSO (20 mL.) was heated to 80°-85° C. for 6 hours to dissolve most of the solids then allowed to cool to room temperature. To the stirred mixture was added 5-bromoindole (2.0 g., 10 mmol.) followed in 1 hour by methyliodide (0.62 mL., 10 mmol.). After stirring for an additional 3 hours the reaction was shown by TLC analysis to be complete. The reaction mixture was diluted with water then extracted with ether. The extracts were washed 2x with water, dried with $Na_2SO_4$, and concentrated in vacuo to give 2.08 g. of 1-methyl-5-bromoindole as a yellow oil which crystallized on standing.

STEP 1B

Tri(1-Methyl-indol-5-yl)bismuthine

To a solution of 1-methyl-5-bromoindole (5.0 g., 23.8 mmol.) in ether (100 mL.) at −78° C. was added a 1.7M solution of t-butyllithium in pentane (28 mL. 47.6 mmol.). The mixture was stirred at −78° C. for 1 hour. To this mixture was then added a solution of bismuth trichloride (2.36 g., 7.5 mmol.) in THF (25 mL.) via syringe. The cooling bath was maintained for 2 hours then allowed to warm to room temperature overnight. In the morning the mixture was quenched with ice water and the product extracted 2X with toluene. The extracts were combined, washed with water, dried with $Na_2SO_4$, and concentrated in vacuo to a volume of about 30 mL., After chilling in the refrigerator for several hours the solid product was filtered, washed with cold toluene and vacuum dried to give tri(1-methyl-indol-5-yl)bismuthine (1.7 g.) as a mustard color solid.

STEP 1C

42-(1-N-Methyl-5-indolyl)oxy-rapamycin

To a stirred solution of tri(1-methylindol-5-yl)bismuthine (450 mg., 0.75 mmol.) (STEP 1B) in $CH_2Cl_2$ (10 mL.) is added peracetic acid (0.158 mL., 0.75 mmol. 32% in acetic acid) followed in 15 minutes by rapamycin (350 mg) and $Cu(OAc)_2$. The mixture is stirred at room temperature for 2 days. The reaction is quenched with saturated aqueous $NaHCO_3$ and the product extracted 3× with $CH_2Cl_2$. The extracts are combined, dried over anhydrous $Na_2SO_4$, filtered, and concentrated in vacuo. The product is isolated and purified 2× by preparative TLC to give 203 mg. of the title compound.

EXAMPLE 2

42-(1-N-Methyl-indol-5-yl)oxy-rapamycin

To a stirred solution of tri(1-methylindol-5-yl)bismuthine (350 mg., 0.584 mmol.) in $CH_2Cl_2$ (6 mL.) is added peracetic acid (0.15 mL., 0.74 mmol., 32% in acetic acid) followed in 15 minutes by rapamycin (0.32 mmol) and $Cu(OAc)_2$ (5 mg., 0.138 mmol.). The reaction mixture is stirred for 2 days at room temperature. The reaction is quenched with saturated aqueous $NaHCO_3$ and the mixture is extracted 2× with $CH_2Cl_2$. The extracts are combined, dried with $Na_2SO_4$, filtered and concentrated in vacuo. The product is isolated by flash column chromatography on silica gel followed by preparative TLC to give of the title compound.

EXAMPLE 3

42-(1-N-Methylindol-5-yl)oxy-rapamycin

To a stirred solution of tri(1-methylindol-5-yl)bismuthine (35 mg., 0.058 mmol.) in $CH_2Cl_2$ (0.7 mL) is added peracetic acid (0.015 mL., 0.074 mmol., 32% in acetic acid) followed in 15 minutes by rapamycin (0.032 mmol.) and $Cu(OAc)_2$ (5 mg., 0.03 mmol.). The reaction mixture is stirred for 3 days at room temperature. The reaction is quenched with saturated aqueous $NaHCO_3$ and is extracted 2× with $CH_2Cl_2$. The extracts are combined, dried with $Na_2SO_4$, filtered and concentrated in vacuo. The product is isolated and purified by preparative TLC on silica gel to give the title compound.

EXAMPLE 4

Tri (Indol-5-yl)bismuthine

A solution of 5-bromoindole (5.0 g., 25.5 mmol.) in ether (50 mL.) was slowly added, at 0° C., to a slurry of KH (2.8 g., 25 mmol., 35% in oil; washed 3× with hexanes) in ether (40 mL.). The reaction mixture was stirred for 20 minutes then chilled to −78° C. A precooled solution of t-butyllithium (29.7 mL., 50.5 mmol., 1.7M in pentane) was added dropwise via syringe to the mixture followed in 40 minutes by a solution of $BiCl_3$ (1.89 g., 6.0 mmol.) in THF (25 mL.). The cooling bath was maintained for 2 hours then allowed to warm to room temperature overnight. The reaction was quenched with ice water and extracted 3× with toluene. The extracts were combined, dried with $Na_2SO_4$, filtered and concentrated in vacuo. The residue was diluted with 75 mL. of toluene then stored at 4° C. overnight. The solids were filtered and air dried to give 1.53 g of tri(indol-5-yl)bismuthine.

STEP 4B

42-(Indol-5-yl)oxy-3-rapamycin

To a stirred solution of tri(indol-5-yl)bis-muthine (1.3 g., 2.33 mmol.), prepared by procedures outlined in STEP 1B in $CH_2Cl_2$ (30 mL.) is added peracetic acid (0.50 mL., 2.31 mmol., 32% in acetic acid) followed in 10 minutes by rapamycin (1.26 mmol) and $Cu(OAc)_2$ (100 mg., 0.55 mmol.). The reaction mixture is allowed to stir at room temperature for 3 days. The reaction is quenched with saturated aqueous $NaHCO_3$ and the mixture extracted 2× with $CH_2Cl_2$. The extracts are combined, dried with $Na_2SO_4$, filtered and concentrated in vacuo. The product is isolated and purified by preparative TLC to give the title compound.

EXAMPLE 5

42-(1-Ethylindol-5-yl)oxy-3-rapamycin

To a stirred solution of tri(1-ethylindol-5-yl)bismuthine (150 mg., 0.23 mmol.), prepared by procedures outlined in STEP 1A and B, in $CH_2Cl_2$(3 ml) is added peracetic acid (0.063 mL., 0.3 mmol., 32% in acetic acid) followed in 15 minutes by rapamycin (0.126 mmol) and $Cu(OAc)_2$ (20 mg., 0.11 mmol.). The reaction mixture is allowed to stir at room temperature for 3 days. The reaction is then quenched with saturated aqueous $NaHCO_3$ and the mixture extracted 2× with $CH_2Cl_2$. The extracts are combined, dried with $Na_2SO_4$, filtered, and concentrated in vacuo to a brown oil. The product is isolated and purified by preparative TLC on silica gel to give the title compound.

EXAMPLE 6

42-(1-Propylindol-5-yl)oxy-3-rapamycin

To a stirred solution of tri(1-propylindol-5-yl)bismuthine (200 mg., 0.29 mmol.), prepared by procedures analogous to STEP 1A and B, in $CH_2Cl_2$ (3 mL.) is added peracetic acid (0.075 mL., 0.36 mmol., 32% in acetic acid) followed in 10 minutes by rapamycin (0.19 mmol) and $Cu(OAc)_2$ (30 mg., 0.17 mmol.). The reaction mixture is stirred for 20 hours at room temperature. The reaction is then quenched with saturated aqueous $NaHCO_3$ and the mixture extracted with $CH_2Cl_2$. The extracts are combined, dried with $Na_2SO_4$, filtered and concentrated in vacuo. The product was isolated and purified by preparative TLC on silica gel to give the title compound.

EXAMPLE 7

42-(1-Hydroxyethylindol-5-yl)oxy-rapamycin

STEP 7A

1-(2-Hydroxyethyl)-5-bromoindole

A mixture of NaOH (4.4 gm, 0.011 mol) in DMSO (175 ml) was stirred at 100° C. for 5 hours at which time it was cooled to 20° C. To this mixture was added 5-bromoindole (20 gm, 0.102 mol) and the reaction was stirred for 8 hours at room temperature. A solution of ethylene oxide (5.1 gm, 0.125 mol) in DMSO (20 ml) was prepared by bubbling the gas into DMSO. To the bromoindole reaction mixture was slowly added the ethylene oxide solution and stirring was continued for another 2.5 hours. The reaction mixture was then poured into ice water and extracted twice with diethyl ether. The combined ether extracts were concentrated in vacuo whereupon crystallization took place. The crude product was recrystallized from diethyl ether:-hexanes (3:2) to afford the title compound (6.25 gm).

STEP 7B 1-(2-t-Butyldimethylsilyloxyethyl)-5-bromoindole

A solution of 1(2-hydroxyethyl)-5-bromoindole (6 gm, 0.025 mol), t-butyldimethylsilyl chloride (4.5 gm, 0.03 mol) and triethylamine (4.2 ml, 0.03 mol) in $CH_2Cl_2$ (60 ml) was stirred for 12 hours at room temperature. The reaction mixture was then washed twice with $H_2O$, dried over $Na_2SO_4$, filtered and concentrated in vacuo to provide the title compound as a yellow oil. $^1H$ NMR was consistent with the desired structure.

STEP 7C

Tri[1-(2-t-Butyldimethylsilyloxyethyl)-indol-5-yl]bismuthine

To a solution of 1(2-t-butyldimethylsilyloxyethyl)-5-bromoindole (1.4 gm, 0.004 mol) in diethyl ether (14 ml) at −78° C. was added t-butyl lithium (4.7 ml of a 1.7M solution in pentanes, 0.008 mol). After stirring for o1.5 hours, a solution of bismuth trichloride (0.4 gm, 0.013 mol) in THF (4 mL) was added. The reaction was stirred at −78° C. for 2 hours and then allowed to warm slowly to room temperature and stirring was continued a further 8 hours. The reaction mixture was then poured into $H_2O$ and extracted with toluene. The combined organic extracts were dried over $Na_2SO_4$, filtered and the filtrate was concentred in vacuo. Purification by chromatography (silica, 4:1, hexanes:ethyl acetate) provided the title compound (1.03 gm) as a semisolid $^1H$ NMR was consistent with desired structure.

STEP 7D 42-(1-t-Butyldimethylsilyloxyethylindol-5-yl)oxyrapamycin

To a solution of tri[1-(2-t-butyldimethylsilyloxyethyl)-indol-5-yl]bismuthine (200 mg) in $CH_2Cl_2$ (200 ml) at room temperature was added peracetic acid (38 μL). After stirring for 10 minutes, rapamycin (150 mg) was added to the reaction mixture followed by $Cu(OAc)_2$ (0.25 gm) and the reaction mixture was stirred for 40 hours. To the reaction mixture was then added saturated $NaHCO_3$ and it was then extracted with $CH_2Cl_2$. The organic extracts were dried over $Na_2SO_4$, filtered and the filtrate was concentrated in vacuo. The crude product was purified by chromatography (silica, 3:1, hexanes:ethyl acetate) to provide the title compound (170 mg). $^1H$ NMR was consistent with desired structure.

STEP 7E 42-(1-Hydroxyethyl-indol-5-yl)oxy-rapamycin

To a solution of 42-(1-t-butyldimethylsilyloxyethylindol-5-yl)oxy-rapamycin (0.17 gm) in $CH_2Cl_2$ (13 ml) at room temperature was added a solution of para-toluene sulfonic acid (15 mg) in $CH_3OH$ (13 ml). The reaction mixture was stirred for 3 hours until TLC (silica, 2:1, hexanes:ethyl acetate) verified that reaction was complete. The reaction mixture was poured into saturated $NaHCO_3$ and extracted twice with $CH_2Cl_2$. The combined organic extracts were dried over $Na_2SO_4$, filtered and concentrated in vacuo. The crude product was purified by chromatography (silica, 2:1 hexanes:ethyl acetate) to provide the title compound 50 mg.

EXAMPLE 8

42-(1'-Allylindol-5'-yl)oxy-rapamycin

STEP 8A

1-Allyl-5-bromoindole

To a stirred mixture of NaOH (204 mg., 5.1 mmol., 1 eq.) in DMSO (10 mL.) was added 5-bromoindole (1.0 g., 5.1 mmol., 1 eq.). The solution was stirred for three hours upon complete dissolution of the NaOH (approximately 1 h.). To this solution was added allyl iodide (0.466 mL., 5.1 mmol., 1 eq.) via syringe. After 2 h. the mixture was diluted with water and extracted 2×with diethyl ether. The organic extracts were combined, dried over anhydrous $MgSO_4$, filtered and concentrated in vacuo. The product was purified by flash column chromatography on silica gel (4:1 hexanes/acetone) affording 730 mg 1-allyl-5-bromoindole.

STEP 8B

Tri(1-Allylindol-5-yl)bismuthine

To a stirred solution of 1-allyl-5-bromoindole (730 mg., 3.09 mmol., 1 eq.) in diethyl ether (15 mL) at −78° C. under $N_2$ was added t-butyllithium (1.8 mL., 3.09 mmol., 1 eq., 1.7M solution in pentane). The mixture was stirred at −78° C. under $N_2$ for 1 h. To this mixture was added a solution of bismuth trichloride (292 mg., 0.93 mmol., 0.3 eq.) in dry THF (3 mL.) dropwise via syringe. The ice bath was packed with dry ice and the flask covered. The mixture was allowed to warm slowly to room temperature overnight. The reaction mixture was then diluted with toluene and washed with brine. The layers were separated and the aqueous layer extracted 3×with toluene. The organic extracts were combined, dried over anhydrous $Na_2SO_4$, filtered and concentrated in vacuo. The residue was dissolved in ether and filtered through a 0.4 micron pTFE membrane. The product started to crystallize. Cooled solution in freezer. Collected crystals giving 200 mg. of tris-1-allylindol-5-yl)bismuthine.

STEP 8C (1'-Allylindol-5'-yl)oxy-rapamycin

To a stirred solution of tri(1-allylindol-5-yl)bismuthine (186 mg., 0.275 mmol., 1.2 eq.) in $CH_2Cl_2$ (3 mL) is added peracetic acid (0.064 mL., 0.303 mmol., 1.32 eq., 32% solution in dilute acetic acid). To this solution is added THF (1 mL.), rapamycin (0.229 mmol.) and copper(II)acetate (10 mg., 0.055 mmol., 0.24 eq.). The mixture is capped and stirred overnight. The reaction is diluted with saturated aqueous $NaHCO_3$ and extracted 4×with $CH_2Cl_2$. The organic extracts are combined, dried over anhydrous $Na_2SO_4$, filtered and concentrated in vacuo. The product was isolated and purified by flash column chromatography on silica gel followed by preparative TLC to afford the title compound.

EXAMPLE 9

42-(9'-Methylcarbazol-3'-yl)oxy-rapamycin

STEP 9A

Tri(9-Methylcarbazol-3-yl)bismuthine

To a stirred mixture of 3-bromo-9-methylcarbazole carbazole (646 mg., 2.48 mmol., 1 eq.) in diethyl ether 12 mL) at −78° C. (not all carbazole in solution) under N₂ was added t-butyllithium (3.0 mL., 4.96 mmol., 2 eq., 1.7M solution in pentane). The mixture was warmed quickly to room temperature and then quickly cooled to −78° C. and stirred under N₂ for 40 minutes. To this mixture was added a solution of bismuth trichloride (235 mg., 0.744 mmol., 0.3 eq.) in dry THF (2.5 mL.) dropwise via syringe. The ice bath was packed with dry ice and the flask covered. The mixture was allowed to warm slowly to room temperature overnight. The reaction mixture was poured into a separatory funnel containing brine and etracted 4×with CH₂Cl₂. The organic extracts were combined, dried over anhydrous Na₂SO₄, filtered and concentrated in vacuo. The solid residue was triturated with ether and ether/methanol. The solids were collected giving 200 mg. of tri(9-methylcarbazol-3-yl)bismuthine. The supernatant was saved for further purification.

STEP 9B 42-(9'-Methylcarbazol-3'-yl)oxy-rapamycin

To a stirred mixture of tri(9-methylcarbazol-3-yl)bismuthine (200 mg., 0.267 mmol., 1.2 eq.) in CH₂Cl₂ (3 mL.) and THF (1 mL.) is added peracetic acid (0.062 mL., 0.295 mmol., 1.32 eq., 32% solution in dilute acetic acid). To this solution is added rapamycin (0.222 mmol) and copper(II)acetate (10 mg., 0.055 mmol., 0.24 eq.). The mixture is capped and stirred. The reaction is diluted with saturated aqueous NaHCO₃ and extracted 4×with CH₂Cl₂. The organic extracts are combined, dried over anhydrous Na₂SO₄, filtered and concentrated in vacuo. The product is isolated and purified by flash column chromatography on silica gel followed by preparative to afford the title compound

EXAMPLE 10

42-(1'-Benzylindol-5-yl)oxy-rapamycin

STEP 10A

1-Benzyl-5-bromoindole

To a stirred mixture of NaOH (204 mg., 5.1 mmol., 1 eq.) in DMSO (10 mL.) was added 5-bromoindole (1.0 g., 5.1 mmol., 1 eq.). The solution was stirred for 20 hours upon complete dissolution of the NaOH (approximately 1 h.). To this solution was added benzyl bromide (0.606 mL., 5.1 mmol., 1 eq.) via syringe. After 7 h. the mixture was diluted with water and extracted 4×with diethyl ether. The organic extracts were combined, dried over anhydrous MgSO₄, filtered and concentrated in vacuo. The product was purified by crystallization (ether/hexanes) affording 888 mg of 1-benzyl-5-bromoindole.

STEP 10B

Tri(1-Benzylindol-5-yl)bismuthine

To a stirred mixture of 1-benzyl-5-bromoindole-3 (888 mg., 3.105 mmol., 1 eq.) in diethyl ether (15 mL) at −78° C. (not all indole was in solution) under N₂ was added t-butyllithium (3.65 mL., 6.21 mmol., 2 eq., 1.7M solution in pentane). The mixture was stirred at −78° C. under N₂ for 1 hour. To this mixture was added a solution of bismuth trichloride (294 mg., 0.932 mmol., 0.3 eq.) in dry THF (3 mL.) dropwise via syringe. The ice bath was packed with dry ice and the flask covered. The mixture was allowed to warm slowly to room temperature overnight. The reaction mixture was poured into a separatory funnel containing brine and etracted 4×with CH₂Cl₂. The organic extracts were combined, dried over anhydrous Na₂SO₄, filtered and concentrated in vacuo. The solid residue was triurated with ether. The solids were collected giving 200 mg. of tri(1-benzylidinol-5-yl)-bismuthine. The supernatant was saved for further purification.

STEP 10C 42-(1'-Benzylindol-5-yl)oxy-rapamycin

To a stirred mixture of tri(1-benzylindol-5-yl)-bismuthine (200 mg., 0.241 mmol., 1.2 eq.) in CH₂Cl₂ (3 mL.) and THF (1 mL.) is added peracetic acid (0.060 mL., 0.285 mmol., 1.4 eq., 32% solution in dilute acetic acid). To this solution is added rapamycin (0.202 mmol) and copper(II)acetate (10 mg., 0.055 mmol., 0.24 eq.). The mixture is capped and stirred overnight. The reaction is diluted with saturated aqueous NaHCO₃ and extracted 4×with CH₂Cl₂. The organic extracts are combined, dried over anhydrous Na₂SO₄, filtered and concentrated in vacuo. The product is isolated and purified by flash chromatography to give the title compound.

EXAMPLE 11

Tri[1-2(t-Butyldimethylsilyloxyethyl)-indol-6-yl]-bismuthine

Step A:

6-Bromoindole

To a solution of 4-bromo-2-nitrotoluene (4.3 g., 20 mmol.) in DMF (40 mL.) was added DMF dimethylacetal (7.15 g., 60 mmol.) and pyrrolidine (1.4 g., 20 mmol.). The solution was heated to 110° C. for 4 hr. then cooled to rt. and diluted with ethyl ether. The mixture was washed 3×with water, dried with Na₂SO₄, filtered and the solvent evaporated. The residue was dissolved in 80% aqueous acetic acid (125 mL.) and heated to 75° C. Zinc dust (9.75 g., 150 mmol.) was added gradually over 20 min. The reaction mixture was heated to 85° C. for 2 hr. then cooled to ~35° C. and filtered to remove unreacted zinc. The filtrate was diluted with ethyl ether, washed 3×with water then with saturated aqueous NaHCO₃. The solution was dried with Na₂SO₄, filtered and concentrated in vacuo to ~30 mL. then diluted with hexanes and filtered. The filtrate was concentrated to an off-white solid which was dissolved in hexane, filtered, and concentrated to give 1.65 g. of the title compound as a light green solid.

Step B:

1-(2-t-Butyldimethylsilyloxyethyl)-6-bromoindole

To a slurry of NaH (192 mg., 4.8 mmol., 60% oil dispersion) in DMF (4 mL.) was added, dropwise, a solution of 6-bromoindole (0.85 g., 4.34 mmol.) in DMF (4 mL.). After stirring for 10 min. at rt., 2-t-butyldimethylsiloxyethyl bromide (1.15 g., 4.8 mmol., neat) was added and the mixture stirred for 1.5 hr. The reaction mixture was partitioned between ice water and hexane. The organics were washed 2×with water, dried with Na₂SO₄, filtered and concentrated in vacuo to a dark oil. The product was isolated by flash column chromatography (silica, 4:1 hexanes/acetone) to give 1.04 g. of the title compound as an oil.

Step C: Tri[1-(2-t-Butyldimethylsilyloxyethyl)-indol-6-yl]-bismuthine

To a solution of 1-(2-t-butyldimethylsilyloxyethyl)-6-bromoindole (1.0 g., 2.81 mmol.) in ethyl ether (10 mL.) at −78° C. was added t-butyllithium (3.4 mL., 5.8 mmol., 1.7M in pentane). After stirring for 10 min. a solution of BiCl₃ (285 mg., 0.9 mmol.) in THF (3 mL.) was added. The reaction mixture was stirred for an additional 10 min. at −78° C. then allowed to warm to rt overnight. The reaction mixture was partitioned between ice water and CH₂Cl₂. The organic layer was washed with water, dried with Na₂SO₄ and concen-

EXAMPLE 12

42-(1-t-Butyldimethylsilyloxyethylindol-6-yl)oxy-rapamycin

To a solution of tri[1-(2-t-butyldimethylsilyloxyethyl)-indol-6-yl] bismuthine (0.60 g., 0.58 mmol.) in CH$_2$Cl$_2$ (5 mL.) at room temperature is added peracetic acid (0.080 mL., 32% in acetic acid) followed in 15 minutes by rapamycin (0.44 mmol.) and Cu(OAc)$_2$ (30 mg.). The reaction mixture is stirred for 20 hr. The reaction is then quenched with saturated NaHCO$_3$ and the mixture extracted with CH$_2$Cl$_2$. The organic extracts are combined, dried over Na$_2$SO$^4$, filtered, and concentrated in vacuo. The product is isolated and purified by preparative TLC on silica gel to give the title compound.

EXAMPLE 13

42-(1-Hydroxyethylindol-6-yl)oxy-rapamycin

To a solution of 42-(1-t-butyldimethylsilyoxyethylindol-6-yl)-oxy-rapamycin (150 mg) in CH$_2$Cl$_2$ (4 mL.) at rt is added a solution of p-toluene sulfonic acid (20 mg.) in CH$_3$OH (4 mL.). The reaction mixture is stirred for 2 hr., quenched with saturated NaHCO$_3$, then extracted with CH$_2$Cl$_2$. The extracts are combined, dried over Na$_2$SO$_4$, filtered and concentrated in vacuo. The product is purified by preparative TLC on silica gel to give the title compound.

EXAMPLE 14

Tri(1-Methylindol-6-yl)bismuthine

To a solution of 1-methyl-6-bromoindole (760 mg., 3.6 mmol.) in ethyl ether (15 mL.) at −78° C. was added t-butyllithium (4.4 mL., 7.5 mmol., 1.7M in pentane). After 10 min. a solution of BiCl$_3$ (375 mg., 1.2 mmol.) in THF (4 mL.) was added and the cooling bath removed. The reaction mixture stirred for 4 hr then poured into ice water and extracted with CH$_2$Cl$_2$. The extracts were combined, backwashed with water, dried with Na$_2$SO$_4$, filtered, and concentrated in vacuo to a dark oil. The product was crystallized from methanol to afford 290 mg. of the title compound as a tan solid.

EXAMPLE 15

42-(1-Methylindol-6-yl)oxy-rapamycin

To a solution of tri[1-methylindol-6-yl]-bismuthine (200 mg., 0.33 mmol.) in CH$_2$Cl$_2$ (2 mL.) at room temperature is added peracetic acid (0.070 mL., 32% in acetic acid) followed in 15 minutes by rapamycin (0.19 mmol.) and Cu(OAc)$_2$ (30 mg.). The reaction mixture is stirred for 4 days. The reaction is then quenched with saturated NaHCO$_3$ and the mixture extracted with CH$_2$Cl$_2$. The organic extracts are combined, dried over Na$_2$SO$^4$, filtered, and concentrated in vacuo. The product is isolated and purified by preparative TLC on silica gel to give the title compound.

EXAMPLE 16

42-(1-Dibenzylphosphonoxy-ethylindol-5-yl)oxy-rapamycin

To a solution of 42-(1-hydroxy-ethylindol-5-yl)oxy-rapamycin (200 mg, azeotroped with toluene) in dry THF is added dibenzyl phosphate 88.6 mg) followed by triphenylphosphine (83.5 mg). The reaction mixture is cooled down to 0° C., then add diethyl azodicarboxylate (50 mL). The reaction mixture is stirred at 0° C. for 5 minutes, remove the ice bath, and stir at room temperature for 2h. The crude reaction mixture is loaded directly onto the silica gel column and purified to give the title compound.

EXAMPLE 17

Monopotassium salt of 42-(1-phosphonoxy-ethylindol-5-yl)oxy-rapamycin

To a solution of 42-(1-dibenzylphosphateethylindol-5-yl)oxy-rapamycin (197 mg) in methanol (3.2 mL) is added potassium bicarbonate (16.3 mg) dissolved in water (200 mL). Add palladium hydroxide over carbon, then charge the reaction mixture with hydrogen via balloon. After the reaction was complete (10 min. by TLC analysis), it is filtered over Celite and rinsed with methanol and small amount of water. The solvent is removed in vacuo, and the crude material is purified on HP-20 column to give the title compound

EXAMPLE 18

42-(1-(N,N-Dimethylglycyloxy)ethylindol-5-yl)oxy-rapamycin

To a solution of 42-(1-hydroxyethylindol-5-yl)oxy-rapamycin (26.6 mg) in dry methylene chloride (0.3 mL) is added hydrochloride salt of N,N-dimethylglycine (5.8 mg), DMAP (3.4 mg) and EDC (8 mg), respectively at room temperature. The reaction mixture is stirred for 4h, then diluted with ethyl acetate and washed with saturated sodium bicarbonate and brine. The organic layer is dried over magnesium sulfate, and the solvent is removed in vacuo. The crude material is purified by flash chromatography to give the title compound.

EXAMPLE 19

42-(1-Succinyloxyethylindol-5-yl)oxy-rapamycin

To a solution of 42-(1-hydroxyethylindol-5-yl)oxy-rapamycin (109 mg) in dry methylene chloride is added succinic anyhydride (11.5 mg) and triethylamine (19 ml). Add DMAP (7 mg) to the reaction mixture and follow the reaction by TLC. The reaction mixture is diluted with ethyl acetate and adjusted to pH 4 with 1N HCl. It is poured into the separatory funnel and the layers are separated. The aqueous layer is extracted with ethyl acetate, and the combined organic layer is washed with brine. It is dried over magnesium sulfate, and the crude material is purified by flash chromatography to give the title compound.

EXAMPLE 20

42-(1-Methyl-3-phenylindol-5-yl)oxy-rapamycin

Step A:

5-Bromo-3-phenylisatin

To a stirred mixture of 5-bromoisatin (5 g., 22.1 mmol., 1 eq.) in dry THF (150 mL.) was added phenylmagnesium bromide (14.7 mL., 44.2 mmol., 2 eq., 3M solution in diethyl ether)(The addition of Grignard reagent was initiated at −78° C. The reaction mixture became too viscous to stir after addition of approximately 5 mL. of the Grignard reagent. The cooling bath was removed and the remainder of the Grignard reagent was added by quick dropwise addition.). The reaction mixture was stirred overnight. Analysis by TLC showed a small amount of unreacted starting material. An additional 1.5 mL. of the Grignard reagent was added and the reaction mixture was stirred an additional 6 hours. The reaction mixture was poured into a separatory funnel containing saturated aqueous ammonium chloride and was extracted 4× with diethyl ether. The organic extracts were combined, dried over anhydrous MgSO$_4$, filtered and concentrated in vacuo. The product was carried on without further purification.

Step B:
5-Bromo-3-phenylindole

To a stirred solution of 5-bromo-3-phenylisatin (6.39 g., 21 mmol., 1 eq.) in dry THF (50 ml.) at 0° C. was added lithium aluminum hydride (2.0 g., 52.5 mmol., 2.5 eq.) portionwise over 1.5 hours. The cooling bath was removed and the reaction was allowed to stir overnight. The mixture was cooled to 0° C. and carefully quenched with 1N aqueous HCl. The mixture was filtered through Celite ™ and the Celite ™ was washed with THF. The filtrate was concentrated in vacuo. dissolved in EtOAc and washed with water. The organic layer was dried over anhydrous MgSO$_4$, filtered and concentrated in vacuo.

Step C:
5-Bromo-1-methyl-3-phenylindole

To a stirred solution of 5-bromo-3-phenylindole (2.4 g., 8.78 mmol., 1 eq.) in dimethylformamide (20 mL.) was added NaH (422 mg. of a 60% dispersion in oil, 10.54 mmol., 1.2 eq.). The mixture was stirred 15 minutes. Methyl iodide (0.6 ml, 9.66 mmol, 1.1 eq) was added via syringe and the reaction mixture was stirred 3 hours. The reaction was quenched with water and extracted 4× with EtOAc. The organic extracts were combined, dried over anhydrous MgSO$_4$, filtered and concentrated in vacuo. The product was purified by flash column chromatography (2:1 hexanes/acetone) giving 1.63 g. 5-bromo-1-methyl-3-phenylindole.

Step D:
Tri(1-Methyl-3-phenylindol-5-yl)bismuthine

To a stirred solution of 5-bromo-1-methyl-3-phenylindole (1.63 g., 5.7 mmol., 1 eq.) in Et$_2$O (35 mL.) at −78° C. under N$_2$ atmosphere was added t-buLi (6.7 mL. of a 1.7M solution in hexanes, 11.4 mmol., 2 eq.) dropwise via syringe. The reaction was stirred 10 minutes at −78° C. To this mixture was added a solution of BiCl$_3$ (540 mg., 1.71 mmol., 0.3 eq.) in THF (7 mL.) dropwise quickly. The reaction was stirred 10 minutes at −78° C. and the cooling bath was removed and the mixture allowed to warm to room temperature. After 3 hours the mixture was poured into a separatory funnel containing water and extracted 4× with CH$_2$Cl$_2$. The organic extracts were combined, dried over anhydrous Na$_2$SO$_4$, filtered and concentrated in vacuo. The residue was triturated with Et$_2$O and the solids collected and washed with Et$_2$O giving 710 mg of Tri(1-methyl-3-phenyl-indol-5-yl)bismuthine.

Step E:
42-(1-Methyl-3-phenylindol-5-yl)oxy-rapamycin

To a stirred solution of tri(1-methyl-3-phenylindol-5-yl)bismuthine (645 mg., 0.78 mmol., 1.2 eq.) in CH$_2$Cl$_2$ (10 mL.) and THF (3 mL.) is added peracetic acid (0.514 mL. of a 32% solution in dilute acetic acid, 0.858 mmol., 1.3 eq.). The mixture is stirred 5 minutes and rapamycin (0.65 mmol., 1 eq.) is added. Cu(OAc)$_2$ (12 mg., 0.065 mmol., 0.1 eq) is added. The flask is capped and the mixture stirred. After 48 hours the reaction is quenched with saturated aqueous NaHCO$_3$ and extracted 4× with CH$_2$Cl$_2$. The organic extracts are combined, dried over anhydrous Na$_2$SO$_4$, filtered and concentrated in vacuo. The product is purified by flash column chromatography on silica gel to give the title compound.

EXAMPLE 21

42-(1-Methyl-3-(2-hydroxyethyl)indol-5-yl)oxy-rapamycin

Step A:
5-Bromo-3-hydroxyethylindole

To a stirred solution of 5-bromoindole-3-acetic acid (1.9 g., 7.48 mmol., 1 eq.) in dry THF (17 mL.) at 0° C. was added lithium aluminum hydride (570 mg. 14.96 mmol., 2 eq.) portionwise over 30 minutes. The reaction mixture coagulated. THF (20 mL.) was added and the cooling bath was removed. The mixture was stirred vigorously. Let stir overnight. The reaction mixture was carefully quenched with 1N aqueous HCl and then acidified with 2N aqueous HCl. The mixture was filtered through Celite ™ and the Celite ™ was washed with THF. The filtrate was concentrated in vacuo, dissolved in EtOAc, and washed with water. The organic layer was dried over anhydrous MgSO$_4$, filtered and concentrated in vacuo. TLC analysis of the residue showed unreacted starting material. The residue was dissolved in Et$_2$O and extracted with 0.25N aqueous NaOH. The organic layer was dried over anhydrous MgSO$_4$, filtered and concentrated in vacuo giving 1.16 g 5-bromo-3-hydroxyethylindole.

Step B:
5-Bromo-3-(2-t-butyldimethylsilyloxy)ethylindole

To a stirred solution of 5-bromo-3-hydroxyethylindole (1.16 g., 4.83 mmol., 1 eq.) in CH$_2$Cl$_2$ (12 mL.) was added triethylamine (1.0 mL., 7.25 mmol., 1.5 eq.) followed by addition of t-butyldimethylchlorosilane (875 mg., 1.2 mmol., 1.2 eq.) and dimethylaminopyridine(catalytic). The mixture was stirred overnight, poured into a separatory funnel containing water and extracted 4× with CH$_2$Cl$_2$. The organic extracts were combined, dried over anhydrous Na$_2$SO$_4$, filtered and concentrated in vacuo giving 1.66 g. 5-bromo-3-(2-t-butyldimethylsilyloxy)ethylindole.

Step C:
5-Bromo-1-methyl-3-(2-t-butyldimethylsilyl-oxy)ethylindole

To a stirred solution of 5-bromo-3-(2-t-butyldimethylsilyloxy)ethylindole (1.66 g., 4.66 mmol., 1 eq.) in DMF (15 mL.) was added NaH (225 mg. of a 60% dispersion in oil, 5.6 mmol., 1.2 eq.). After 15 minutes iodomethane (0.320 mL., 5.13 mmol., 1.1 eq.) was added. The mixture was stirred 4 hours and then poured into a separatory funnel containing water and extracted 2× with EtOAc. The organic extracts were combined, dried over anhydrous MgSO$_4$, filtered and concentrated in vacuo giving 1.49 g. 5-bromo-1-methyl-3-(2-t-butyldimethylsilyloxy)ethylindole.

Step D:
Tri(1-methyl-3-(2-t-butyldimethylsilyloxy)-ethylindol-5-yl)bismuthine

To a stirred solution of 5-bromo-1-methyl-3-(2-t-butyldimethylsilyloxy)ethylindole (1.49 g., 4.03 mmol., leq.) in Et$_2$O (15 mL.) at −78° C. under nitrogen atmosphere was added t-butyllithium (4.8 mL. of a 1.7M solution in pentanes, 8.06 mmol., 2 eq.) dropwise via syringe. The mixture was stirred 10 minutes at −78° C.

and then a solution of BiCl₃ (381 mg., 1.21 mmol., 0.3 eq.) in THF (5 mL.) was added quickly dropwise via syringe. The mixture was stirred for 7 minutes at −78° C. under nitrogen. The cooling bath was removed and the mixture was allowed to warm to room temperature. After 1 hour the mixture was poured into a separatory funnel containing water and extracted 4× with CH₂Cl₂. The organic extracts were combined, dried over anhydrous Na₂SO₄, filtered and concentrated in vacuo giving 554 mg. crude product. $^1$H NMR analysis of the residue indicates mixture of approximately 2:1 of the desired bismuthine to reduced indole. Used the mixture crude in subsequent reaction.

Step E:
42-(1-Methyl-3-(2-t-butyldimethylsilyloxyethyl)indol-5-yl)oxy-rapamycin

To a stirred solution of tri(1-methyl-3-(2-t-butyldimethylsilyloxy)ethylindol-5-yl)bismuthine (554 mg. crude) in CH₂Cl₂ (10 mL.) and THF (3 mL.) is added peracetic acid (0.120 mL. of a 32% solution in dilute acetic acid, 0.571 mmol.) To this mixture is added rapamycin (0.439 mmol.) followed by addition of Cu(OAc)₂ (24 mg., 0.13 mmol.). The reaction mixture is allowed to stir overnight. The mixture is poured into a separatory funnel containing saturated aqueous NaHCO₃ and extracted 4× with CH₂Cl₂. The organic extracts are combined, dried over anhydrous Na₂SO₄, filtered and concentrated in vacuo. The product is purified by flash column chromatography on silica gel to give the title compound.

Step F:
42-(1-Methyl-3-(2-hydroxyethyl)indol-5-yl)oxy-rapamycin

To a stirred solution of 42-(1-methyl-3-(2-t-butyldimethylsilyloxyethyl)indol-5-yl)oxy-rapamycin 0,16-tetraone (200 mg.) in CH₂Cl₂ (6 mL.) and CH₃OH (6 mL.) is added p-toluenesulfonic acid monohydrate (30 mg.). The reaction mixture is allowed to stir 3 hours. The reaction is quenched with saturated aqueous NaHCO₃ and extracted 4× with CH₂Cl₂. The organic extracts are combined, dried over anhydrous Na₂SO₄, filtered and concentrated in vacuo. The product is purified by preparative TLC on silica gel to give the title compound.

EXAMPLE 22

42-(1-(3-Hydroxy-propyl)indol-6-yl)oxy-rapamycin

Step A:
2-t-Butyldimethylslyloxyethyl bromide

To a solution of 2-bromoethanol (50 g, 0.40 mol) in CH₂Cl₂ (50 mL) was added t-butyldimethylchlorosilane (63.4 g, 0.42 mol), triethylamine (45.4 g, 0.45 mol) and dimethylaminopyridine (0.5 g). After stirring overnight the reaction mixture was washed 3× with water. The organic fraction was dried with Na₂SO₄, filtered, and concentrated in vacuo to provide 85 g of the title compound as a light yellow oil.

$^1$H NMR (CDCl₃) δ: 3.85 (t, 2H); 3.36 (t, 2H); 0.86 (s, 9H); 0.05 (s, 6H).

Step B: 1-(2-Butyldimethylsilyloxyethyl)-5-bromoindole

To a slurry of sodium hydride (12 g, 0.3 mol, 60% dispersion in oil) in DMF (200 mL) was added dropwise a solution of 5-bromoindole (50 g, 0.255 mol) in DMF (300 mL). After stirring for 15 minutes 2-t-butyldimethylsilyloxyethyl bromide (60 g, 0.255 mol, neat) was added dropwise and the reaction mixture stirred for 1 hour. The reaction mixture was partitioned between ice water and ethyl ether. The organic fraction was washed with water, dried over Na₂SO₄, filtered and concentrated in vacuo. The product was purified by column chromatography (silica, 3:1 hexane/acetone) to give 68.6 g of the title compound as a light yellow oil.

$^1$H NMR (CDCl₃) δ: 7.72 (s, 1H); 7.1–7.3 (m, 3H); 6.4 (d, 1H); 4.18 (t, 2H); 3.86 (t, 2H); 0.8 (s, 9H); −0.18 (s, 6H).

Step C:
42-(1-(3-t-Butyldimethylsilyloxypropyl)-indol-6-yl)oxy-rapamycin

To a solution of tri[1-(3-t-butyldimethylsiloxypropyl)-indol-6-yl]bismuthine (0.917 gm, crude) in CH₂Cl₂ (7 mL) at room temperature was added peracetic acid (0.10 mL, 32% in acetic acid) followed in 15 minutes by rapamycin (0.63 mmol) and Cu(OAc)₂ (50 mg). The reaction mixture is stirred for 2 days. The reaction is then quenched with saturated NaHCO₃ and the mixture extracted with CH₂Cl₂. The organic extracts are combined, dried over Na₂SO₄, filtered, and concentration in vacuo. The product is isolated and purified by preparative TLC on silica gel to give the title compound.

Step D:
42-(1-(3-Hydroxypropyl)indol-6-yl)-oxy-rapamycin

To a solution of 42-(1-(3-t-butyldimethylsilyloxypropyl)indol-6-yl)oxy-rapamycin (318 mg) in CH₂Cl₂ (5 mL) at rt is added a solution of p-toluene sulfonic acid (25 mg) in CH₃OH (5 mL). The reaction mixture is stirred for 3 hours quenched with saturated NaHCO₃, then extracted with CH₂Cl₂. The extracts are combined, dried over Na₂SO₄, filtered and concentrated in vacuo. The product is purified by preparative TLC on silica gel to give the title compound.

EXAMPLE 23

T-Cell Proliferation Assay

1. Sample Preparation

The compounds to be assayed were dissolved in absolute ethanol at 1 mg/ml.

2. Assay

Spleens from C57B1/6 mice were taken under sterile conditions and gently dissociated in ice-cold RPMI 1640 culture medium (GIBC), Grand Island, N.Y.) supplemented with 10% heat-inactivated fetal calf serum (GIBO)). Cells were pelleted by centrifugation at 1500 rpm for 8 minutes. Contaminating red cells were removed by treating the pellet with ammonium chloride lysing buffer (GIBO)) for 2 minutes at 4° C. Cold medium was added and cells were again centrifuged at 1500 rpm for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 25° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at 2.5×10⁵ cells/ml in complete culture medium composed of RPMI 1640 medium with 10% heat-inactivated fetal calf serum, 100 mM glutamine, 1 mM sodium pyruvate, $2\times10^{-5}$M 2-mercaptoethanol and 50 μg/ml gentamycin. Ionomycin was added at 250 ng/ml and PMA at 10 ng/ml. The cell suspension was immediately distributed into 96 well flat-bottom microculture plates (Costar) at 200 μl/well. The various dilutions of the compound to be tested were then added in triplicate wells at 20 μl/well. The compound 17-allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-aza-tricyclo[22.3.1.0$^{4,9}$]octacos-18-ene-2,3,10,16-tetraone was used as a standard. The culture plates were then incubated at 37° C. in a humidified atmosphere of 5% $CO_2$-95% air for 44 hours. The proliferation of T lymphocytes was assessed by measurement of tritiated thymidine incorporation. After 44 hours of culturing, the cells were pulse-labelled with 2 μCi/well of tritiated thymidine (NEN, Cambridge, Mass.). After another 4 hours of incubation, cultures were harvested on glass fiber filters using a multiple sample harvester. Radioactivity of filter discs corresponding to individual wells was measured by standard liquid scintillation counting methods (Betacounter). Mean counts per minute of replicate wells were calculated and the results expressed as concentration of compound required to inhibit tritiated thymidine uptake of T-cells by 50%.

A selection of compounds were tested according to the previous procedure. The title compound of the following Example had activity in inhibiting the proliferation of T-cells in the aforementioned assay: 7.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound of Formula I:

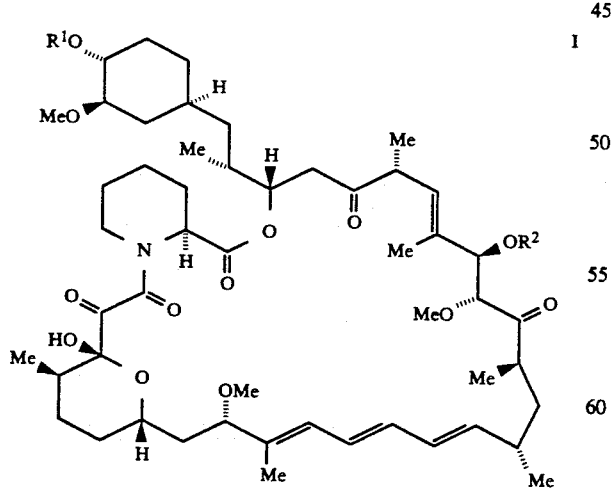

I or a pharmaceutically acceptable salt thereof, wherein:
$R^1$ is selected from:
  (1) heteroaryl, wherein heteroaryl is selected from the group consisting of

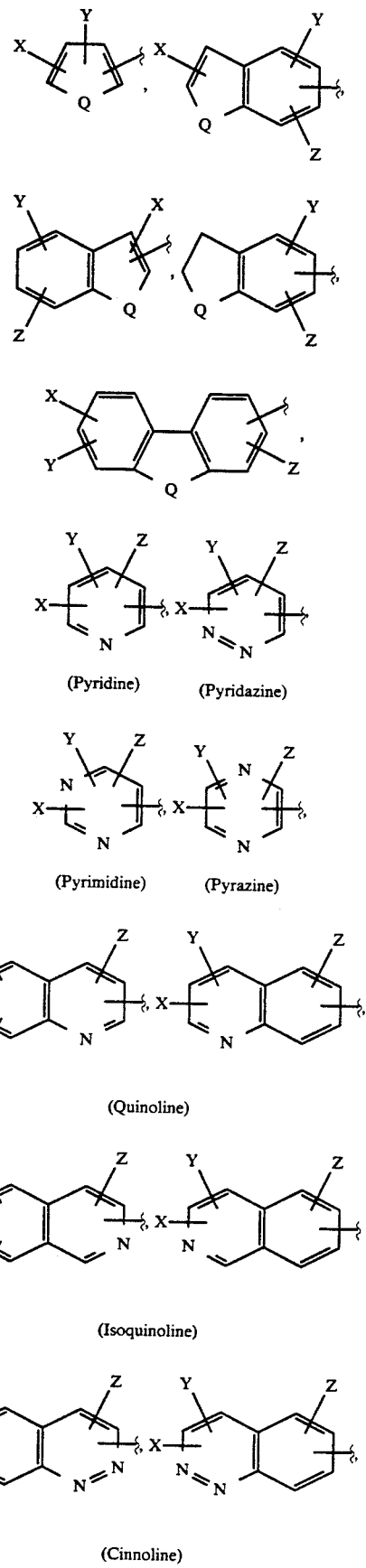

(Pyridine)   (Pyridazine)

(Pyrimidine)   (Pyrazine)

(Quinoline)

(Isoquinoline)

(Cinnoline)

-continued

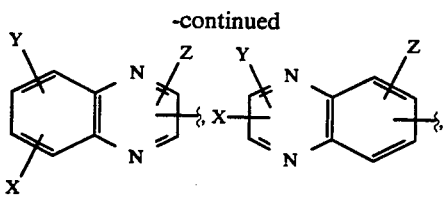

(Quinoxaline)

wherein O is —N(X)—, —O—, or —S—;
(2) substituted heteroaryl, wherein heteroaryl is as defined above, and in which the substituents are X, Y and Z;
(3) heteroaryl-$C_{1-10}$alkyl, wherein heteroaryl is as defined above;
(4) substituted heteroaryl-$C_{1-10}$alkyl, wherein heteroaryl is as defined above and in which the heteroaryl group is substituted by X, Y and Z and the alkyl portion may be substituted with one or more of the substituent(s) selected from:
  (a) hydroxy,
  (b) oxo,
  (c) $C_{1-6}$-alkoxy,
  (d) aryl-$C_{1-3}$alkoxy, wherein aryl is selected from the group consisting of phenyl and naphthyl,
  (e) substituted aryl-$C_{1-3}$alkoxy, wherein aryl is as defined above and in which the substituents on aryl are X, Y and Z,
  (f) unsubstituted or substituted aryloxy, in which the substituents on aryl are X, Y and Z,
  (g) —OCO—$C_{1-6}$alkyl,
  (h) —NR$^6$R$^7$, wherein R$^6$ and R$^7$ are independently selected from
    (i) hydrogen,
    (ii) $C_{1-10}$alkyl unsubstituted or substituted with one or more of the substituent(s) selected from:
      (a') aryl, wherein aryl is as defined above and which is unsubstituted or substituted with X, Y and Z,
      (b') heteroaryl, wherein heteroaryl is as defined above and which is unsubstituted or substituted with X, Y and Z,
      (c') —OH,
      (d') $C_{1-6}$alkoxy,
      (e') —CO$_2$H,
      (f') —CO$_2$—$C_{1-6}$alkyl,
      (g') —$C_{3-7}$cycloalkyl, and
      (h') —OR$^{11}$,
    (iii) $C_{3-10}$alkenyl unsubstituted or substituted with one or more of the substituent(s) selected from:
      (a') aryl, wherein aryl is as defined above and which is unsubstituted or substituted with X, Y and Z,
      (b') heteroaryl, wherein heteroaryl is as defined above and which is unsubstituted or substituted with X, Y and Z,
      (c') —OH,
      (d') $C_{1-6}$alkoxy,
      (e') —CO$_2$H,
      (f') —CO$_2$—$C_{1-6}$alkyl,
    (g') —$C_{3-7}$cycloalkyl, and
    (h') —OR$^{11}$,
    (iv) or where R$^6$ and R$^7$ and the N to which they are attached may form a heterocyclic ring selected from the group consisting of: morpholine, thiomorpholine, piperidine, and piperazine,
  (i) —NR$^6$CO—$C_{1-6}$alkyl-R$^7$, wherein R$^6$ and R$^7$ are as defined above,
  (j) —NR$^6$CO$_2$—$C_{1-6}$alkyl-R$^7$,
  (k) —NR$^6$CONR$^6$R$^7$,
  (l) —OCONR$^6$R$^7$,
  (m) —COOR$^6$,
  (n) —CHO,
  (o) aryl, wherein aryl is as defined above,
  (p) substituted aryl wherein aryl is as defined above and in which the substituents are X, Y and Z,
  (q) —OR$^{11}$, and
  (r) —S(O)$_p$—$C_{1-6}$alkyl;
(5) heteroaryl-$C_{1-10}$alkyl wherein heteroaryl is as defined above and one or more of the alkyl carbons is replaced by a group selected from: —NR$^6$—, —O—, —S(O)$_p$—, —CO$_2$—, —O$_2$C—, —CONR$^6$—, —NR$^6$CO—, —NR$^6$CONR$^7$—;
(6) substituted heteroaryl-$C_{1-10}$alkyl wherein heteroaryl is as defined above and one or more of the alkyl carbons is replaced by a group selected from: —NR$^6$—, —O—, —S(O)$_p$—, —CO$_2$—, —O$_2$C—, —CONR$^6$—, —NR$^6$CO—, and —NR$^6$CONR$^7$—, the heteroaryl group is substituted with X, Y, and Z, and the alkyl group may be substituted with one or more of the substituent(s) selected from:
  (a) hydroxy,
  (b) oxo,
  (c) $C_{1-6}$alkoxy,
  (d) aryl-$C_{1-3}$alkoxy, wherein aryl is as defined above,
  (e) substituted aryl-$C_{1-3}$alkoxy, wherein aryl is as defined above and in which the substituents on aryl are X, Y and Z,
  (f) unsubstituted or substituted aryloxy, wherein aryl is as defined above and in which the substituents on aryl are X, Y and Z,
  (g) —OCO—$C_{1-6}$alkyl,
  (h) —NR$_6$R$^7$, wherein R$^6$ and R$^7$ are as defined above,
  (i) —NR$^6$CO—$C_{1-6}$alkyl-R$^7$,
  (j) —NR$^6$CO$_2$—$C_{1-6}$alkyl-R$^7$,
  (k) —NR$^6$CONR$^6$R$^7$,
  (l) —OCONR$^6$R$^7$,
  (m) —COOR$^6$,
  (n) —CHO,
  (o) aryl, wherein aryl is as defined above,
  (p) substituted aryl wherein aryl is as defined above in which the substituents are X, Y and Z,
  (q) —OR$^{11}$, and
  (r) —S(O)$_p$—$C_{1-6}$alkyl;
(7) heteroaryl-$C_{3-10}$alkenyl wherein heteroaryl is as defined above and alkenyl contains one to four double bonds;
(8) heteroaryl-$C_{3-10}$alkenyl wherein heteroaryl is as defined above and alkenyl contains one to four double bonds and wherein one or more of the alkyl carbons is replaced by a group selected from: —NR$^6$—, —O—, —S(O)$_p$—, —CO$_2$—, —O$_2$C—, —CONR$^6$—, —NR$^6$CO—, and —NR$^6$CONR$^7$—;
(9) substituted heteroaryl-$C_{3-10}$alkenyl wherein heteroaryl is as defined above and alkenyl contains one to four double bonds and wherein one or more of the alkyl carbons may be replaced by a group selected from: —NR$^6$—, —O—, —S(O)$_p$—, —CO$_2$—, —O$_2$C—, —CONR$^6$—, —NR$^6$CO—, and —NR⁶CONR⁷, the heteroaryl group is substituted with X, Y, and Z, and the alkyl group may be substituted with one or more of the substituent(s) selected from:
- (a) hydroxy,
- (b) oxo,
- (c) $C_{1-6}$alkoxy,
- (d) aryl-$C_{1-3}$alkoxy, wherein aryl is as defined above,
- (e) substituted aryl-$C_{1-3}$alkoxy, wherein aryl is as defined above and in which the substituents on aryl are X, Y and Z,
- (f) unsubstituted or substituted aryloxy, wherein aryl is defined above and in which the substituents on aryl are X, Y and Z,
- (g) —OCO—$C_{1-6}$alkyl,
- (h) —NR⁶R⁷, wherein R⁶ and R⁷ as defined above,
- (i) —NR⁶CO—$C_{1-6}$alkyl, wherein R⁶ is as defined above,
- (j) —NR⁶CO₂—$C_{1-6}$alkyl,
- (k) —NR⁶CONR⁶R⁷,
- (l) —OCONR⁶R⁷,
- (m) —COOR⁶,
- (n) —CHO,
- (o) aryl, wherein aryl is as defined above,
- (p) substituted aryl wherein aryl is as defined above and in which the substituents are X, Y and Z, and
- (q) —OR¹¹, and
- (r) —S(O)$_p$—$C_{1-6}$alkyl;

R² is selected from:
- (1) the definitions of R¹;
- (2) hydrogen;
- (3) phenyl;
- (4) substituted phenyl in which the substituents are X, Y and Z;
- (5) 1-or 2-naphthyl;
- (6) substituted 1- or 2-naphthyl in which the substituents are X, Y and Z;
- (7) biphenyl;
- (8) substituted biphenyl in which the substituents are X, Y and Z;
- (9) $C_{1-10}$alkyl;
- (10) substituted-$C_{1-10}$alkyl in which one or more substituent(s) is(are) selected from:
  - (a) hydroxy,
  - (b) oxo,
  - (c) $C_{1-6}$alkoxy,
  - (d) aryl-$C_{1-3}$alkoxy, wherein aryl is as defined above,
  - (e) substituted aryl-$C_{1-3}$alkoxy, wherein aryl is as defined above and in which the substituents on aryl are X, Y and Z,
  - (f) unsubstituted or substituted aryloxy, in which the substituents on aryl are X, Y and Z,
  - (g) —OCO—$C_{1-6}$alkyl,
  - (h) —NR⁶R⁷, wherein R⁶ and R⁷ are as defined above
  - (i) —NR⁶CO—$C_{1-6}$alkyl-R⁷, wherein R⁶ and R⁷ is as defined above,
  - (j) —COOR⁶, wherein R⁶ is as defined above,
  - (k) —CHO,
  - (l) phenyl,
  - (m) substituted phenyl in which the substituents are X, Y and Z,
  - (n) 1- or 2-naphthyl,
  - (o) substituted 1- or 2-naphthyl in which the substituents are X, Y and Z,
  - (p) biphenyl,
  - (q) substituted biphenyl in which the substituents are X, Y and Z,
  - (r) —OR¹¹, and
  - (s) —S(O)$_p$—$C_{1-6}$alkyl;
- (11) $C_{3-10}$alkenyl;
- (12) substituted $C_{3-10}$alkenyl in which one or more substituent(s) is(are) selected from:
  - (a) hydroxy,
  - (b) oxo,
  - (c) $C_{1-6}$alkoxy,
  - (d) phenyl-$C_{1-3}$alkoxy,
  - (e) substituted phenyl-$C_{1-3}$alkoxy, in which the substituents on phenyl are X, Y and Z,
  - (f) —OCO—$C_{1-6}$alkyl,
  - (g) —NR⁶R⁷, wherein R⁶ and R⁷ are as defined above
  - (h) —NR⁶CO—$C_{1-6}$alkyl, wherein R⁶ is as defined above,
  - (i) —COOR⁶, wherein R⁶ is as defined above,
  - (j) —CHO,
  - (k) phenyl,
  - (l) substituted phenyl in which the substituents are X, Y and Z,
  - (m) 1- or 2-naphthyl,
  - (n) substituted 1- or 2-naphthyl in which the substituents are X, Y and Z,
  - (o) biphenyl,
  - (p) substituted biphenyl in which the substituents are X, Y and Z,
  - (q) —OR¹¹, and
  - (r) —S(O)$_p$—$C_{1-6}$alkyl;
- (13) $C_{3-10}$alkynyl;
- (14) substituted $C_{3-10}$alkynyl in which one or more substituent(s) is(are) selected from:
  - (a) hydroxy,
  - (b) oxo,
  - (c) $C_{1-6}$alkoxy,
  - (d) phenyl-$C_{1-3}$alkoxy,
  - (e) substituted phenyl-$C_{1-3}$alkoxy, in which the substituents on phenyl are X, Y and Z,
  - (f) —OCO—$C_{1-6}$alkyl,
  - (g) —NR⁶R⁷, wherein R⁶ and R⁷ are as defined above,
  - (h) —NR⁶CO—$C_{1-6}$alkyl, wherein R⁶ is as defined above,
  - (i) —COOR⁶, wherein R⁶ is as defined above,
  - (j) —CHO,
  - (k) phenyl,
  - (l) substituted phenyl in which the substituents are X, Y and Z,
  - (m) 1- or 2-naphthyl,
  - (n) substituted 1-or 2-naphthyl in which the substituents are X, Y and Z,
  - (o) biphenyl,
  - (p) substituted biphenyl in which the substituents are X, Y and Z,
  - (q) —OR¹¹; and
- (15) —R¹¹;

R¹¹ is selected from:
- (a) —PO(OH)O⁻M⁺, wherein M⁺ is a positively charged inorganic or organic counterion selected from the group consisting of: ammonium, sodium, lithium, potassium, calcium, magnesium, dicyclohexylamine, N-methyl-D-glucamine, arginine and lysine,
- (b) —SO₃⁻M⁺,
- (c) —CO(CH₂)$_q$CO₂⁻M⁺, wherein q is 1-3, and (d) —CO—C$_{1-6}$alkyl-NR$^6$R$^7$, wherein R$^6$ and R$^7$ are as defined above and the alkyl is unsubstituted or substituted with one or more substituents selected from:
  (i) hydroxy,
  (ii) C$_{1-6}$alkoxy,
  (iii) —NR$^{16}$R$^{17}$, wherein R$^{16}$ and R$^{17}$ are independently selected from:
    (a') hydrogen, and
    (b') C$_{1-6}$alkyl,
  (iv) —COOR$^6$, wherein R$^6$ is as defined above,
  (v) phenyl,
  (iv) substituted phenyl in which the substituents are X, Y and Z,
  (vii) heteroaryl, wherein heteroaryl is as defined above,
  (viii) —SH, and
  (ix) —S—C$_{1-6}$alkyl;
X, Y and Z independently are selected from:
  (a) hydrogen,
  (b) C$_{1-10}$alkyl, unsubstituted or substituted with one or more substituents selected from:
    (i) aryl, wherein aryl is as defined above,
    (ii) substituted aryl wherein aryl is as defined above and in which the substituents are X', Y' and Z',
    (iii) heteroaryl, wherein heteroaryl is as defined above,
    (iv) substituted heteroaryl wherein heteroaryl is s defined above and in which the substituents are X', Y', and Z',
    (v) unsubstituted or substituted aryloxy, wherein aryl is as defined above and in which the substituents on aryl are X', Y' and Z',
    (vi) —OR$^6$,
    (vii) —OR$^{11}$,
    (viii) —OCOR$^6$,
    (ix) —OCO$_2$R$^6$,
    (x) —NR$^6$R$^7$,
    (xi) —CHO,
    (xii) —NR$^6$COC$_{1-6}$alkyl-R$^7$,
    (xiii) —NR$^6$CO$_2$C$_{1-6}$alkyl-R$^7$,
    (xiv) —NR$^6$CONR$^6$R$^7$,
    (xv) —OCONR$^6$R$^7$,
    (xvi) —CONR$^6$R$^7$,
  (c) C$_{1-10}$alkyl wherein one or more of the alkyl carbons is replaced by a group selected from —NR$^6$—, —O—, —S(O)$_p$—, —CO$_2$—, —O$_2$C—, —CONR$^6$—, —NR$^6$CO—, —NR$^6$CONR$^7$—, —CO—, —CH(OH)—, alkenyl or alkynyl and the alkyl may be unsubstituted or substituted with one or more substituents selected from:
    (i) aryl, wherein aryl is as defined above,
    (ii) substituted aryl wherein aryl is as defined above and in which the substituents are X', Y' and Z',
    (iii) heteroaryl, wherein heteroaryl is as defined above,
    (iv) substituted heteroaryl wherein heteroaryl is as defined above and in which the substituents are X', Y', and Z',
    (v) unsubstituted or substituted aryloxy, wherein aryl is as defined above and in which the substituents on aryl are X', Y', and Z',
    (vi) —OR$^6$,
    (vii) —OR$^{11}$,
    (viii) —OCOR$^6$,
    (ix) —OCO$_2$R$^6$,
    (x) —NR$^6$R$^7$,
    (xi) —CHO
    (xii) —NR$^6$COC$_{1-6}$alkyl-R$^7$,
    (xiii) —NR$^6$CO$_2$C$_{1-6}$alkyl-R$^7$,
    (xiv) —NR$^6$CONR$^6$R$^7$,
    (xv) —OCONR$^6$R$^7$,
    (xvi) —CONR$^6$R$^7$,
  (d) halogen,
  (e) —NR$^6$R$^7$,
  (f) —CN,
  (g) —CHO,
  (h) —CF$_3$,
  (i) —SR$^8$, wherein R$^8$ is hydrogen, C$_{1-6}$alkyl, trifluoromethyl, or phenyl,
  (j) —SOR$^8$,
  (k) —SO$_2$R$^8$,
  (l) —CONR$^6$R$^7$,
  (m) R$^9$O(CH$_2$)$_m$- wherein R$^9$ is hydrogen, C$_{1-6}$alkyl, hydroxy-C$_{2-3}$alkyl, —CF$_3$, phenyl, R$^{11}$ or naphthyl and m is 0, 1, 2, or 3,
  (n) —CH(OR$^{12}$)(OR$^{13}$), wherein R$^{12}$ and R$^{13}$ are C$_{1-3}$alkyl or taken together form an ethyl or propyl bridge,
  (o)

$$R^9\overset{O}{\underset{\|}{C}}O(CH_2)_m-$$

wherein R$^9$ and m are as defined above,
  (p)

$$R^9O\overset{O}{\underset{\|}{C}}(CH_2)_m-$$

wherein R$^9$ and m are as defined above, and
  (q) —R$^{11}$;
  or any two of X, Y and Z may be joined to form a ring selected from the group consisting of dioxolanyl, and dioxanyl;
X', Y' and Z' independently are selected from:
  (a) hydrogen,
  (b) C$_{1-7}$alkyl,
  (c) C$_{2-6}$alkenyl,
  (d) halogen,
  (e) —(CH$_2$)$_m$—NR$^6$R$^7$, wherein R$^6$, R$^7$ and m are as defined above,
  (f) —CN,
  (g) —CHO,
  (h) —CF$_3$,
  (i) —SR$^8$, wherein R$^8$ is hydrogen, C$_{1-6}$alkyl, trifluoromethyl, or phenyl,
  (j) —SOR$^8$, wherein R$^8$ is as defined above,
  (k) —SO$_2$R$^8$, wherein R$^8$ is as defined above,
  (l) —CONR$^6$R$^7$, wherein R$^6$ and R$^7$ are as defined above,
  (m) R$^9$O(CH$_2$)$_m$- wherein R$^9$ and m are as defined above,
  (n) —CH(OR$^{12}$)(OR$^{13}$), wherein R$^{12}$ and R$^{13}$ are as defined above,
  (o)

wherein R$^9$ and M are as defined above,
  (p)

wherein R[9] and M are as defined above, and
(q) —R[11].
2. The compound of claim 1, wherein the heteroaryl is selected from the group consisting of:
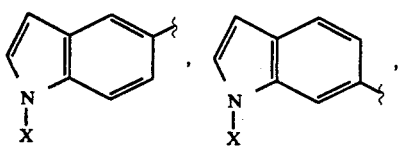
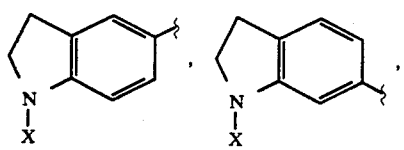
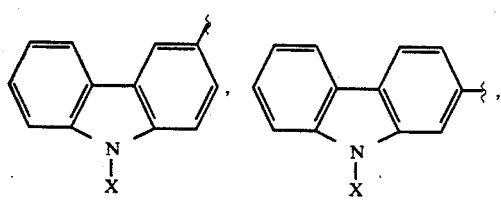
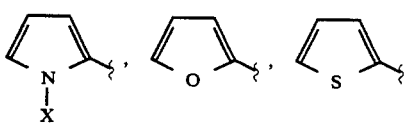
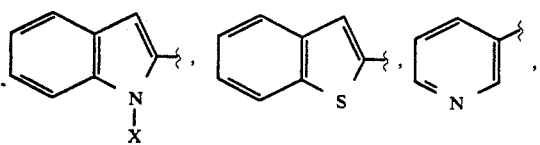
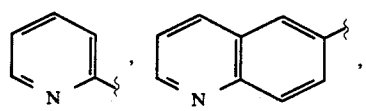
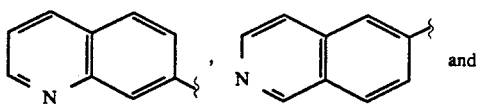
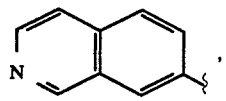
wherein X is as defined in claim 1.
3. The compound of claim 1, wherein heteroaryl is:
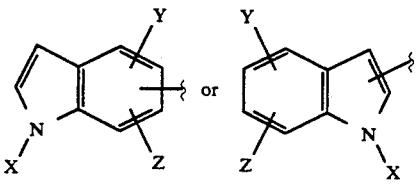
4. A compound which is:
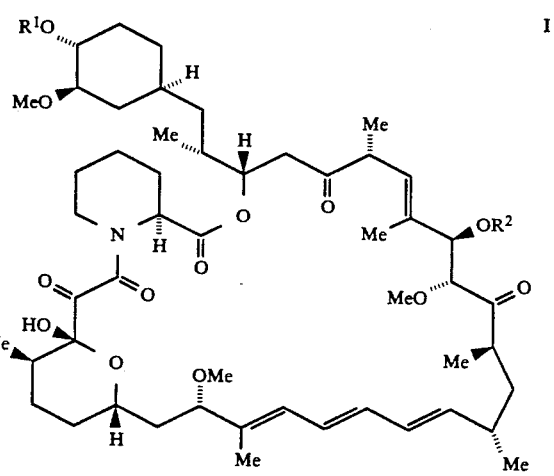
wherein R[1] and R[2] are selected from the following combinations of substituents:
| | R[1] | R[2] |
|---|---|---|
| (a) | 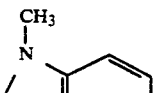 | H |
| (b) | H | 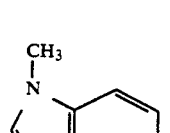 |

-continued
| | R¹ | R² |
|---|---|---|
| (c) | 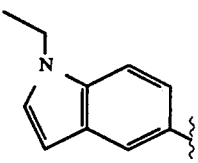 | H |
| (d) | 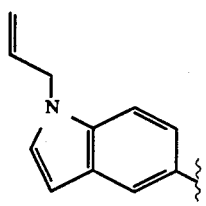 | H |
| (e) | 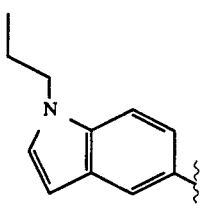 | H |
| (f) | H |  |
| (g) | H | 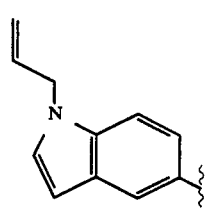 |
| (h) | H | 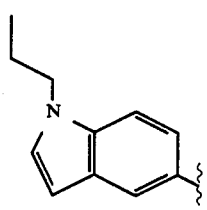 |
| (i) | 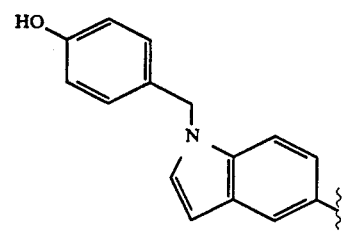 | H |

-continued
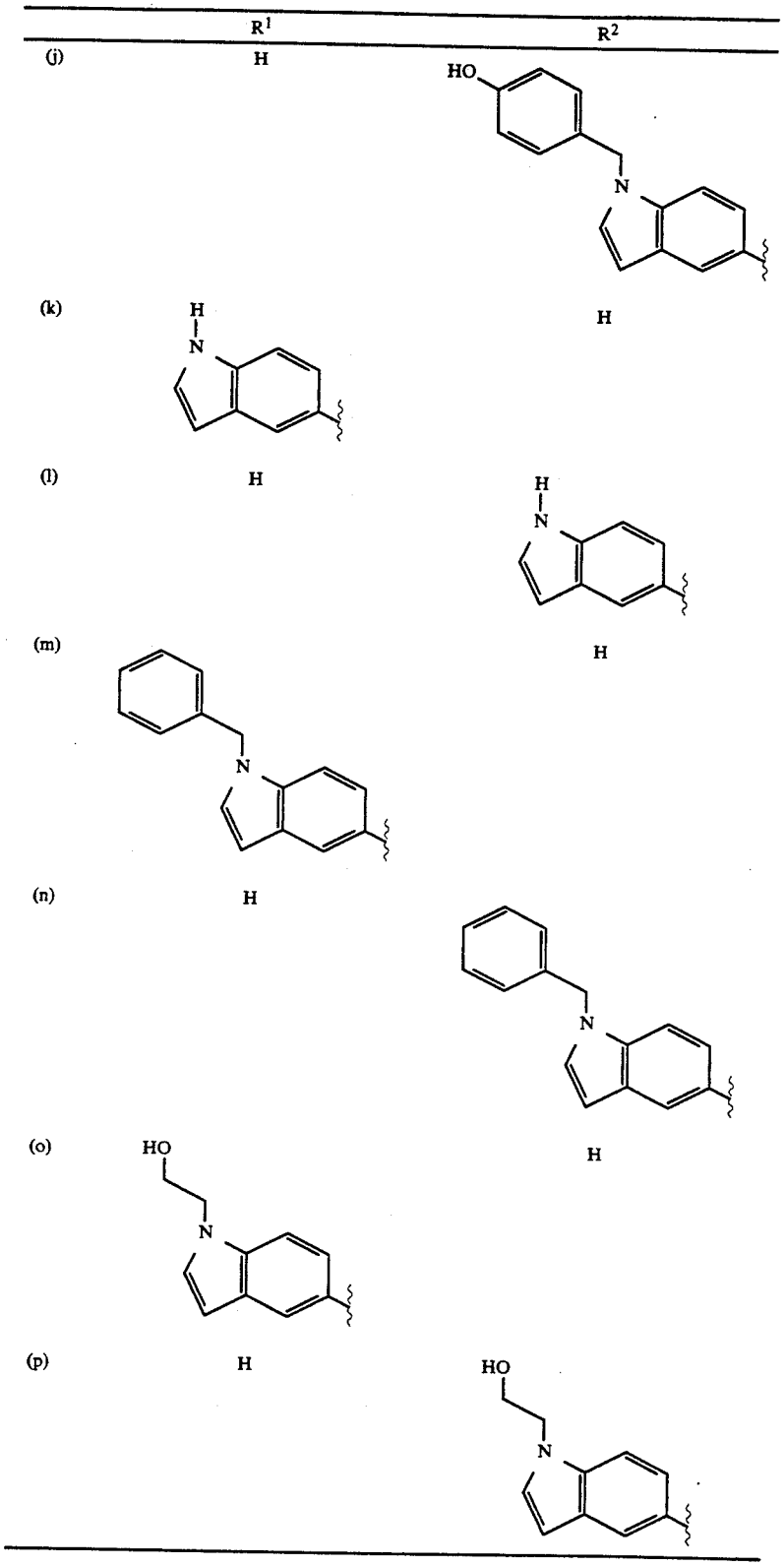
5. A compound which is: 42-(1-hydroxyethyl-indol-5-yl)oxy rapamyein.
* * * * *